US006861659B2

(12) United States Patent
Tanabe

(10) Patent No.: US 6,861,659 B2
(45) Date of Patent: *Mar. 1, 2005

(54) METHOD OF INSPECTING UNUNIFORMITY OF TRANSPARENT MATERIAL, APPARATUS THEREFOR, AND METHOD OF SELECTING TRANSPARENT SUBSTRATE

(75) Inventor: Masaru Tanabe, Yamanashi-ken (JP)

(73) Assignee: Hoya Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/421,431

(22) Filed: Apr. 23, 2003

(65) Prior Publication Data

US 2003/0218145 A1 Nov. 27, 2003

Related U.S. Application Data

(63) Continuation of application No. 09/254,849, filed as application No. PCT/JP98/03200 on Jul. 16, 1997, now Pat. No. 6,610,994.

(30) Foreign Application Priority Data

| | | |
|---|---|---|
| Jul. 17, 1997 | (JP) | 9-192763 |
| Sep. 29, 1997 | (JP) | 9-263456 |
| Oct. 30, 1997 | (JP) | 9-298727 |
| Dec. 26, 1997 | (JP) | 9-360331 |

(51) Int. Cl.$^7$ ..................... G01N 21/86

(52) U.S. Cl. ..................... 250/559.4; 250/559.45

(58) Field of Search ..................... 250/559.4, 559.42, 250/559.45; 356/239.1, 239.2, 239.3

(56) References Cited

U.S. PATENT DOCUMENTS 3,988,068 A * 10/1976 Sprague ..................... 356/124
5,355,213 A 10/1994 Dotan
5,627,638 A 5/1997 Vokhmin
6,555,273 B2 * 4/2003 Tanabe ..................... 430/5
6,610,994 B1 * 8/2003 Tanabe ..................... 250/559.45

FOREIGN PATENT DOCUMENTS

| | | |
|---|---|---|
| EP | 0 497 649 | 8/1992 |
| JP | 8-261953 | 10/1996 |
| WO | WO 99/04249 | 1/1999 |

OTHER PUBLICATIONS

International Search Report of Oct. 6, 1998 for PCT/JP98/03200.
European Search Report of EP 98 93 2551 dated Feb. 13, 2002.
English abstract: Japanese patent application no. 5–87739 to Kowa Co., Apr. 6, 1993.
English abstract: Japanese patent application no. 58–162038 to Canon K.K., Sep. 26, 1983.
English abstract: Japanese patent application no. 6–82392 to NHK Spring Co., Ltd., Mar. 22, 1994.

* cited by examiner

*Primary Examiner*—Que T. Le
(74) *Attorney, Agent, or Firm*—Cook, Alex, McFarron, Manzo, Cummings & Mehler, Ltd.

(57) ABSTRACT

A laser beam L from a laser 2 is introduced from an introducing surface into a transparent substrate 1 by using mirrors 31 and 32. The laser beam introduced through the transparent substrate 1 repeats a total reflection on the surfaces (main surfaces and end surfaces) of the transparent substrate 1 and enters a state in which the laser beam is almost confined in the substrate 1. When an ununiform portion such as a scratch exists on the surface of the transparent substrate 1, however, total reflecting conditions are not satisfied and the light leaks out of the ununiform portion. The leaked light is formed as an image on a CCD 6 by a lens system 7 and an image process is executed by an image processing apparatus 12. In a detected image, the ununiform portion in which the scratch or the like exists is brightly seen in a linear or a dot form in a black background, so that the ununiform portion such as a very fine scratch can be detected.

10 Claims, 19 Drawing Sheets

| INCIDENT ANGLE | NUMBER OF REFLECTING TIMES ON T PLANE | NUMBER OF REFLECTING TIMES ON SURFACE | Z COORDINATE UPON EMITTING |
|---|---|---|---|
| 42.90 | 23 | 594 | 6.21 |
| 42.95 | 23 | 593 | 0.10 |
| 43.00 | 19 | 489 | 0.00 |
| 43.05 | 13 | 334 | 6.31 |
| 43.10 | 17 | 436 | 6.34 |
| 43.15 | 5 | 128 | 6.28 |
| 43.20 | 9 | 230 | 6.24 |
| 43.25 | 2 | 51 | 0.16 |
| 43.30 | 15 | 382 | 6.21 |
| 43.35 | 26 | 661 | 0.10 |
| 43.40 | 29 | 736 | 6.35 |
| 43.45 | 3 | 76 | 6.32 |
| 43.50 | 24 | 607 | 0.14 |
| 43.55 | 4 | 101 | 0.09 |
| 43.60 | 5 | 126 | 6.27 |
| 43.65 | 19 | 478 | 6.28 |

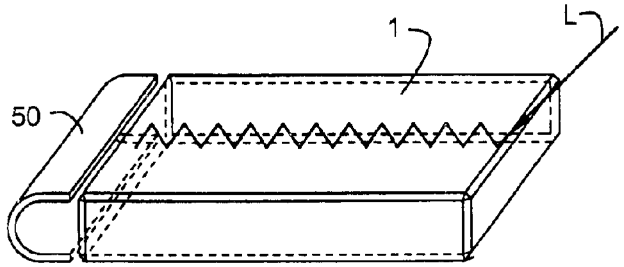
FIG. 26 (1)
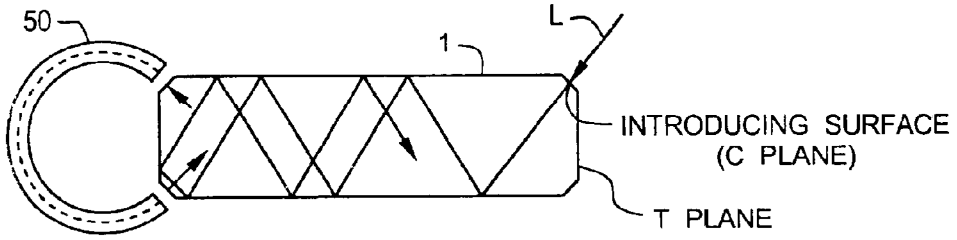
FIG. 26 (2)

METHOD OF INSPECTING UNUNIFORMITY OF TRANSPARENT MATERIAL, APPARATUS THEREFOR, AND METHOD OF SELECTING TRANSPARENT SUBSTRATE

CROSS-REFERENCE TO RELATED APPLICATION

This application is a continuation of U.S. Ser. No. 09/254,849, filed May 24, 1999 and issuing as U.S. Pat. No. 6,610,994, issuing on Aug. 26, 2003, which is a 371 of PCT/JP98/03200 filed Jul. 6, 1997.

TECHNICAL FIELD

The present invention relates to a method of inspecting an optical ununiformity (defect) of a transparent material such as a glass substrate serving as a transparent substrate for a photo mask or a transparent substrate for an information recording medium and an apparatus therefore. More particularly, the invention relates to a method of inspecting an ununiformity of a transparent material and an apparatus therefore, whereby the ununiformity of the transparent material can be detected at a high sensibility and a high speed by using characteristics of a total reflection on the surface of the transparent material and its apparatus.

BACKGROUND ART

In a manufacturing process of a semiconductor integrated circuit, a photo mask, or the like, a photolithography method is used to form a fine pattern. For example, when the semiconductor integrated circuit is manufactured, a pattern is transferred onto a transparent substrate which was mirror-finished by polishing at a high precision by using a photo mask whose pattern was formed by a transparent film (for example, a chromium film). As a method of inspecting the photo mask which can be said as an original board of the pattern, as shown in a surface state inspecting apparatus disclosed in Japanese Patent Application Laid-Open No. 58-162038 (1983), a method of converging light onto a fine region on a pattern surface and comparing a reflection output and transmission output from the pattern surface has been known.

In recent years, however, in association with a realization of high density of the pattern, in addition to the inspection for the pattern surface similar to the above method, a fine defect of the transparent substrate itself which was mirror-finished by polishing at a high precision is also regarded as a target of the defect detection. In the above-mentioned method, since the light is converged onto the fine region on the pattern surface, when an inspecting region extends over a wide range, it is necessary to scan the light by using some means, a long inspecting time is required in proportional to the area of the inspecting region, and a change in light quantity of the reflection light and transmission light for the pattern itself and transparent substrate is not large depending on the presence or absence of the defect, so that it is difficult to apply the method to the detection of the fine defect on the transparent substrate.

Also with regard to a transparent substrate for an information recording medium, from the viewpoints of the formation of an under layer and a magnetic layer having a good crystallinity which are formed on the surface of the transparent substrate, the low flotation of a magnetic head, and the like with the realization of high density recording, the transparent substrate having the surface polished at a-high precision is required, so that the fine defect of the transparent substrate itself is also set to a target of the defect detection. However, existing defect inspecting method and apparatus do not necessarily satisfy a request of the defect detection.

According to the invention, therefore, in order to solve the above problems, it is an object to provide a method of inspecting an ununiformity of a transparent material, whereby an optical ununiformity of the transparent material can be certainly detected at a high precision and a high speed and an apparatus therefore.

Further, an object of the invention is to provide a method of inspecting an ununiformity of a transparent material, whereby a desired transparent material can be immediately extracted and an apparatus therefore.

FIG. 26 shows diagrams showing another embodiment for the ununiformity inspection of the invention;

DISCLOSURE OF THE INVENTION

Figure 1:
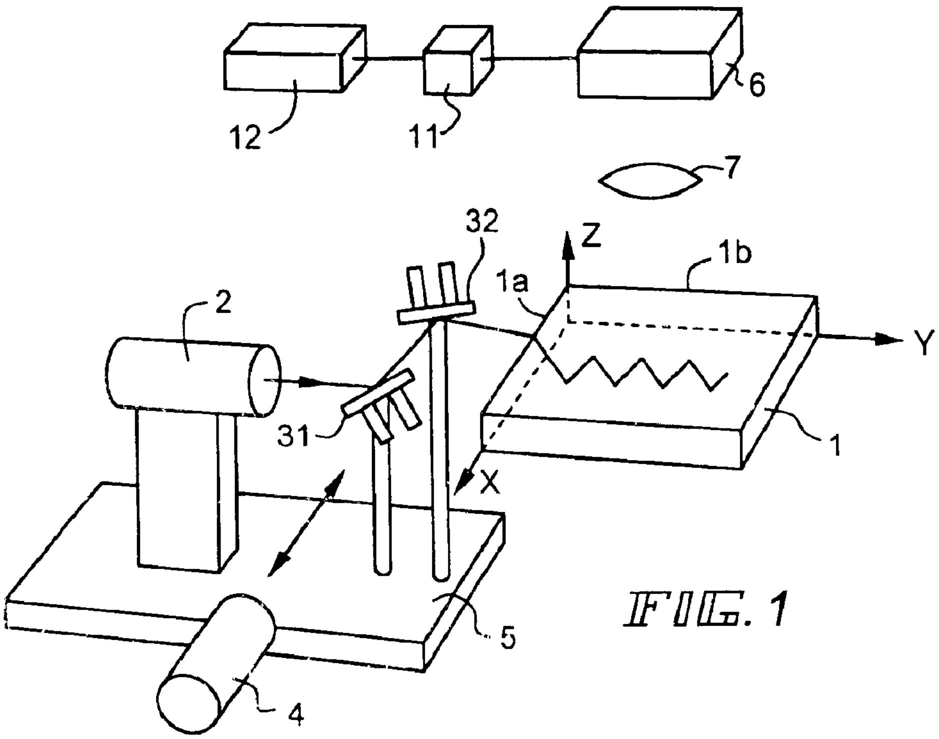
FIG. 1 is a schematic constructional diagram showing an embodiment of an apparatus for inspecting an ununiformity of a transparent material according to the invention.

According to the invention, there is provided a method of inspecting an ununiformity of a transparent material by introducing a laser beam into the transparent material, wherein the transparent material has: at least one pair of total reflective surfaces in which the laser beam introduced in the transparent material repeats the total reflection and which face each other and at least one pair of turning surfaces which are arranged so as to face each other in the progressing direction of the laser beam that repeats the total reflection between the total reflective surfaces and progresses and which totally reflect the laser beam and return to the total reflective surfaces, when an optical path in the transparent material is optically uniformed, the laser beam is introduced in such a manner that the laser beam which propagates in the transparent material and impinges on the total reflective surfaces and the turning surfaces of the transparent material is propagated so as to totally reflect and repeat between at least the pair of turning surfaces and the laser beam is spread in an inspecting region which is formed by the propagation and is surrounded by the total reflective surfaces and the turning surfaces, and when an ununiform portion exists in the optical path of the laser beam which is introduced into the transparent material and propagates, light that leaks out of the total reflective surfaces and/or the turning surfaces is detected, thereby inspecting an ununiformity of the transparent material.

When there is no ununiform portion such as a scratch on the surface in the transparent material, the laser beam introduced through the transparent material repeats the total reflection on the surface and is confined in the transparent material (the laser beam is spread), so that the light does not substantially leak to the outside (on the total reflective surfaces and turning surfaces). When the ununiform portion exists in the transparent material, however, the total reflecting conditions are not satisfied and the light leaks out of the surface of the transparent material. That is, when the ununiform portion (defect) such as scratch, crack, and stain due to an adhering foreign matter exists on the surface of the transparent material, the light leaks out of the surfaces (total reflective surfaces and turning surfaces) as total reflective surfaces so long as the optical path is uniform. In addition to the ununiformity of the surface of the transparent material, also with respect to the detection of a defect such as internal scratch, crack, or foreign matter such as bubbles or a defect of the glass in which a transmission is the same but a reflective index alone is different, which fact is peculiar to the striae of the glass, light is out of the optical path (passage) where the light inherently passes if it is uniform in the scratch or a portion where the refractive index is different, the total reflecting conditions on the surface are not satisfied, and the light leaks to the outside of the transparent material, so that it can be detected.

As mentioned above, according to the inspecting method of the invention, since the light is (substantially) confined in the transparent material by using the geometrical and optical total reflection serving as a physical critical phenomenon, responses to inspection light in the ununiform and uniform portions of the transparent material as an inspecting object are also critical, so that the ununiformity appears as a dramatic contrast. That is, the inspecting method of the invention can be called as an inspecting method for the defect (ununiformity) by a light confining method. A defect such as a very fine scratch of the transparent material is observed as light in a shielding case like a black box leaks out of a pinhole existing on the case.

Incident conditions of the light for repeating the total reflection on the surface of the transparent material to (substantially) confine the light in the transparent material are obtained as follows. The conditions to (substantially) confine the light by the multiple total reflection in a rectangular transparent material like a transparent substrate will now be obtained hereinbelow.

Figure 27:
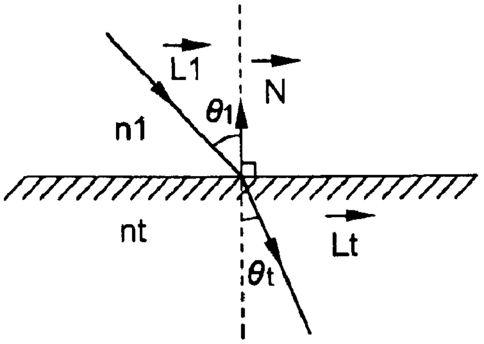
FIG. 27 is a diagram showing a refraction of light on boundary surfaces having different refractive indices.

Prior to the obtaining of the conditions to confine the light, first, as shown in FIG. 27, the direction of refraction light when the light impinges on a medium such as glass having transparency of a refractive index nt from a medium such as air of a refractive index ni is obtained (although a vector is expressed by a normal arrow in the diagram, a vector A is expressed as <A> in the document).

As shown in FIG. 27, a refraction beam <Lt> when an incident beam <Li> impinges on a boundary surface between the refractive indices ni and nt is considered. A solvent vector which is perpendicular to the boundary surface and is directed to the side of an incident medium is set to <N> (unit vector). The vector <Lt> of the refraction beam exists on the flat surface extended by the vectors <N> and <Li> and can be expressed by a linear connection of <N> and <Li>. That is, it can be expressed as follows.

$$\langle Lt\rangle=\alpha\langle Li\rangle+\beta\langle N\rangle \qquad (1)$$

Where, $\alpha$ and $\beta$ are coefficients. In order to simplify a calculation, when it is assumed that the vectors <Li> and <Lt> are set to unit vectors, the following equations are satisfied.

$$\langle Li\rangle\cdot\langle Li\rangle=1,\ \langle Lt\rangle\cdot\langle Lt\rangle=1 \tag{2}$$

When a law of refraction (Snell's law) is applied to the refraction on the boundary surface, since an incident angle is θi and a refractive angle is θt, $$\sin\theta t=(ni/nt)\sin\theta i \tag{3}$$

When θi and θt are expressed by vectors, $$\langle Li\rangle\cdot\langle N\rangle=|\langle Li\rangle|\cdot|\langle N\rangle|\cos(\pi-\theta i)=-\cos\theta i \tag{4}$$

$$\langle Lt\rangle\cdot\langle N\rangle=|\langle Lt\rangle|\cdot|\langle N\rangle|\cos(\pi-\theta t)=-\cos\theta t \tag{5}$$

An object which will now be obtained is the refraction beam vector <Lt>. When $\alpha$ and $\beta$ of the equation (1) are determined, <Lt> is decided. Therefore, when $\alpha$ and $\beta$ are expressed by using ni, nt, and θi from the equations (1) to (5), $$\alpha=ni/nt$$

$$\beta=-\{1-(ni/nt)^2(1-\cos^2\theta 1)\}^{\frac{1}{2}}+(ni/nt)\cos\theta i$$

The direction of the refraction beam <Lt> to the incident beam <Li> is determined.

Subsequently, conditions under which the refraction beam introduced in the predetermined direction as mentioned above repeats the total reflection on the surface of the rectangular transparent material and is confined in the transparent material will now be obtained.

Figure 28:
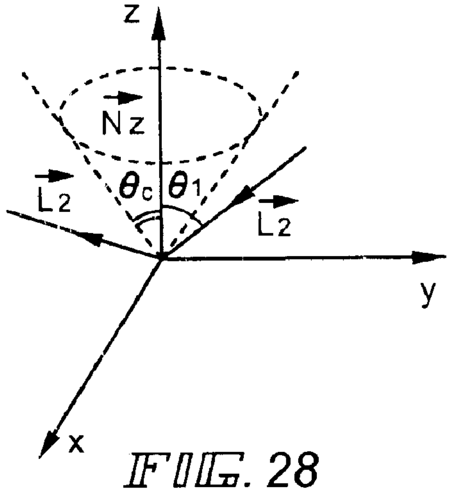
FIG. 28 is a diagram used to obtain total reflecting conditions on the surface of a transparent material.

First, an xy plane is considered as a first boundary surface of the total reflection. As shown in FIG. 28, when it is assumed that a normal vector in the positive direction of a z axis is set to <Nz>=(0, 0, 1) and an incident vector <L1> (unit vector)=(L1x, L1y, L1z) impinges on the xy plane at the incident angle θi, the following equation is satisfied.

$$\langle Li\rangle\cdot\langle Nz\rangle=\cos(\pi-\theta 1)$$

When the equation is expanded, $$L1z=-\cos\theta 1$$

Since |<L1>|=1, the following equation is satisfied under conditions that when θ1≧θc.

$$L1x^2+L1y^2+\cos^2\theta 1=1 \tag{6}$$

It is sufficient that the incident vector which can totally reflect on the xy plane of the first boundary surface exists on the outside of a circular cone in FIG. 28 obtained by rotating a straight line which forms a critical angle θc with the z axis around the z axis. The vectors which can satisfy the above-mentioned conditions infinitely exist.

Since the vector reflects on the xy plane, the vector <L2> after completion of the reflection is as follows.

$$\langle L2\rangle=(L1x,\ L1y,\ -L1z)$$

-continued $$=(L1x,\ L1y,\ \cos\theta 1)$$

Further, it is necessary to consider conditions under which the vector <L2> totally reflects on a second boundary surface. When it is assumed that the second boundary surface is set to an xz plane and the vector impinges on the xz plane at an incident angle θ2, $$\langle L2\rangle\cdot\langle Ny\rangle=\cos(\pi-\theta 2)$$

Where, <Ny> denotes a unit vector (0, 1, 0) which is directed to the positive direction of a y axis. When the above equation is expanded, $$L1y=-\cos\theta 2$$

From the above equation and equation (6), it is necessary to satisfy the following equation under conditions that when θ1, θ2≧θc.

$$L1x^2=1-\cos^2\theta 1-\cos^2\theta 2 \tag{7}$$

Since the vector reflects on the xz plane, a vector <L3> after completion of the reflection is as follows.

$$\langle L3\rangle=(+\{1-\cos^2\theta 1-\cos^2 2\}^{1/2}\cdot\cos\theta 2,\ \cos\theta 1)$$

When the vector <L3> totally reflects on a third boundary surface, the confinement of the light is succeeded. When the third boundary surface is set to a yz plane and the vector impinges on the yz plane at an incident angle θ3, $$\langle L3\rangle\cdot\langle Nx\rangle=\cos(\pi-\theta 3)$$

Where,Nx=(1, 0, 0). Therefore, the above equation is expanded to $L3x=-\cos\theta 3$, so that it is necessary to satisfy the expression of $+\{1-\cos^2\theta 1-\cos^2\theta 2\}^{1/2}=-\cos\theta 3$, that is, $$\cos^2\theta 1+\cos^2\theta 2+\cos^2\theta 3=1 \tag{8}$$

sin(π/2)=(nt/ni)sin θc at the boundary angle θc. Therefore, when ni=1.00, nt=1.47, since sin θc=1/1.47, the boundary angle θc=42.9°.

When θ1=θ2=θ3, according to the equation (8), 3 $\cos^2$ θ1=1 and θ1=54°, such an equation of θ1≧54°>θc=42.9° is sufficiently satisfied. A margin having a degree of freedom in the above-mentioned conditions can be utilized as a degree of freedom which allow the total reflection to more occur on a specific reflective surface. As for substrate glass, it is sufficient to select <L1> so as to reduce the reflection at the end surface.

As mentioned above, the conditions under which the light is confined by the multiple total reflection are as follows.

$$\cos^2\theta 1+\cos^2\theta 2+\cos^2\theta 3=1$$

$$\cos\theta c\geqq\cos\theta 1,\ \cos\theta 2,\ \cos\theta 3>0$$

Figure 29:
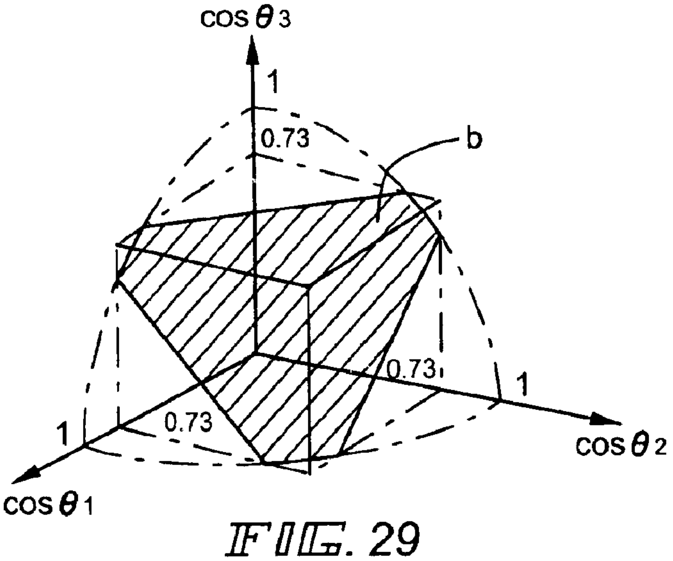
FIG. 29 is a diagram showing a region satisfying the total reflecting conditions under which the light is confined in a rectangular transparent material by a multiple total reflection.

When θc=42.9°, cos θc=0.73. Therefore, when a region where θ1, θ2, and θ3 are satisfied is shown in the diagram by using cos θ1, cos θ2, and cos θ3 as axes of coordinates, as shown in FIG. 29, a curved surface 60 serving as a surface of a sphere whose radius is equal to 1 in a cube whose side is equal to 0.73 is the region to satisfy the total reflecting conditions.

Although the total reflecting conditions with respect to the rectangular transparent material like a transparent substrate has been derived, it is also possible to decide the conditions of the incident angle of the light by a method similar to the above in a general form which will be described hereinlater. The conditions of the incident angle of the light which is introduced into the transparent material in the embodiment, which will be described hereinlater, are derived on the basis of the above.

In the method of inspecting the ununiformity of the invention, the transparent material can take any form of a square (rectangular) plate, a circular plate, an annular plate, a lens whose curved surface has a large curvature, a sphere, a polyhedron, a column, a cylinder, and a polyhedral column. When it is possible to realize a state where the light repeats the reflection of the number of predetermined times or more in at least the inspecting region of the transparent material and the light is confined in the transparent material, the form of the transparent material is not limited.

As mentioned above, in order to confine the light in the transparent material, it is preferable that the transparent material has at least one pair of total reflective surfaces In which the light introduced through the transparent material repeats the total reflection and which face each other and at least one pair of turning surfaces which are arranged so as to face each other in the progressing direction of the laser beam that repeats the total reflection between the total reflective surfaces and propagates and which totally reflect and return the laser beam to the total reflective surfaces. Particularly, the turning surfaces are important to confine the light in the transparent material. The turning surfaces have to be provided so as to face each other in the progressing direction of the light and it is necessary to provide at least one pair. The reason is that if the light does not repeat between the turning surfaces, the light cannot be confined.

As for the introduction of the laser beam, it is necessary to introduce the laser beam in such a manner that the laser beam introduced through the transparent material is propagated so that light which propagates in the transparent material and impinges on the total reflective surfaces and turning surfaces totally reflects and repeats between at least the pair of turning surfaces and the laser beam is spread in an inspecting region which is formed by the propagation and is surrounded by the total reflective surfaces and the turning surfaces. That is, when the optical path in the transparent material is optically uniform, the laser beam is introduced in such a manner that the light introduced through the transparent material is propagated while repeating the total reflection between the total reflective surfaces which face each other, the light impinges on a turning surface (a) and totally reflects, after that, the light further repeats the propagation in the transparent material and totally reflects between at least one of turning surfaces (b), (c), . . . except for the turning surface (a), and the light propagated in the turning surface (a) is again returned. In this case, the optical path in the transparent material is optically uniform. Even if there is no ununiform portion, the total reflection is repeated between the total reflective surfaces and turning surfaces. Since there is no singular point that the light leaks on the total reflective surfaces and turning surfaces (except for the region to introduce the laser beam), the confinement of the light is (substantially) realized. In case of one pair of the turning surfaces, the light is confined on one certain plane of the transparent material. In case of a plurality of pairs of the turning surfaces, the confinement of the light is executed in almost the whole region of the transparent material.

In order to (substantially) confine the light in the transparent material, it is sufficient to introduce the laser beam so that such a singular point that the laser beam geometrically and optically leaks does not substantially exist on the total reflective surfaces and the turning surfaces. Since it is "geometrically and optically", light such as Rayleigh scattering light derived by an optical change due to a feature that is peculiar to the transparent material is not considered as an introduced laser beam here. The reason why "such a singular point that the laser beam leaks does not substantially exist" is that a case where after the laser beam repeats the total reflection many times between the total reflective surfaces and the turning surfaces, a very slight laser beam does not satisfy the total reflecting conditions and leaks out of the transparent material due to an influence of a spread angle of the laser beam itself. Therefore, it is "substantially" in consideration of the case is considered. Since the leak light due to the spread angle of the laser beam itself leaks in the direction along the surface of the transparent material, it is not detected by detecting means, so that it has no effect on a detecting sensitivity.

In order to confine the light in the transparent material, when it is assumed that the refractive index of the transparent material to a wavelength $\lambda$ of the laser beam which is introduced is set to nt, the refractive index of the external medium which is come into contact with the transparent material is set to ni, and an angle of the light which impinges on the total reflective surfaces and turning surfaces is set to $\theta ik$ (k denotes a position where the laser beam impinges on the total reflective surfaces and turning surfaces after it is introduced through the transparent material and the incident positions are is sequentially set as k=1, 2, . . . ), it is sufficient to introduce the laser beam so that $\theta ik$ is equal to a critical angle $\theta$ expressed as $\sin \theta = ni/nt$ or more in the total reflective surfaces and turning surfaces.

As for the surface of the transparent material, with regard to a form in which it is difficult to confine the light by the total reflection (for example, a form whose curved surface has a large curvature), the ununiformity can be inspected by propagating the light so as to repeat the total reflection on at least two pairs of surfaces (at least one pair of total reflective surface and at least one pair of turning surfaces) which are provided on the outside of the transparent material and which face each other. Specifically speaking, the inspection can be executed in such a manner that a transparent vessel having mirror-finished surfaces is used, a transparent material is inserted into a medium (a liquid or the like) in the vessel, which has a refractive index larger than that of an external medium of the vessel, and the laser beam is introduced so as to repeat the total reflection on the external surface of the vessel and propagate.

It is preferable that by introducing the laser beam so that all of the laser beams totally reflect on at least the total reflective surfaces and turning surfaces on which the laser beam introduced through the transparent material first impinges, the light satisfying the total reflecting conditions can be precisely introduced through the transparent material. In a case other than the above, for example, when scattered light propagates in the transparent material on the surface to introduce the laser beam, since loci of (a plurality of) beams which will propagate in the transparent material cannot be expected, it is difficult that almost all of the introduced laser beams which impinges on the total reflective surfaces and turning surfaces totally reflect, so that the confinement of the light as shown in the invention is not realized.

It is desirable that an introducing surface to introduce the laser beam is provided in a portion sandwiched by one certain total reflective surface and at least one turning surface. As for the introduction of the laser beam to the transparent material, the laser beam can be introduced from the total reflective surface or turning surface other than the introducing surface. In this case, however, as an entrance window to introduce the laser beam, an optical member made of a material having substantially the same refractive index as that of the transparent material has to be attached by an adhesive agent or the like, so that it takes much time. Since the optical member is attached to the total reflective surfaces or turning surfaces serving as inspecting regions, the light propagated in the transparent material does not satisfy the total reflecting conditions in the attached portion and the light leaks, so that the inspection cannot be substantially executed. Therefore, it is not preferable.

As mentioned above, when the introducing surface to introduce the laser beam exists, as specific introducing means, the laser beam is introduced so as to emit the introduced laser beam into only the introducing surface and a surface in which an angle formed between the surface and introducing surface is almost equivalent to an angle formed between the surface and total reflective surface, thereby realizing the light confinement referred to in the present invention.

It is desirable that at least the introducing surface of the transparent material to introduce the laser beam is mirror-polished. The laser beam is introduced so that the total reflection is repeated at the total reflective surfaces and turning surfaces and the light is confined. When the introducing surface is mirror-polished, however, the introduced laser beam is not influenced due to a diffusion by the introducing surface and is propagated as parallel light as it is. Consequently, all of the light which impinges on the total reflective surfaces and turning surfaces are totally reflected, so that responses of the inspection light in the ununiform and uniform portions of the transparent material become more critical and the contrast is improved. Preferably, it is desired that the whole surface (total reflective surfaces, turning surfaces, and introducing surfaces) of the transparent material is mirror-polished.

It is assumed that the size of the total reflective surface is set to L, the width of introducing surface is set to d, the refractive index of the transparent material for the wavelength $\lambda$ of the laser beam is set to nt, the refractive index of the external medium which is come into contact with the transparent material is set to ni, a beam diameter of the laser beam is set to $\phi$, the angle of the light incident on the total reflective surfaces and the turning surfaces is set to $\theta$ik (k denotes the position where the laser beam first impinges on the total reflective surfaces and turning surfaces after the laser beam is introduced through the transparent substrate and the incident positions are sequentially set as k=1, 2, . . . Particularly, an angle of the light which first impinges on the total reflective surface or turning surface after the laser beam is introduced is set to $\theta$i.), and the number of reflecting times at the total reflective surfaces is set to m. When m is expressed by a function of L, d, nt($\lambda$), ni, $\phi$, and $\theta$1, it is preferable that conditions of at least one of L, d, nt($\lambda$), ni, $\phi$, and $\theta$1 are determined so that m is equal to a reference set value or more in a range where each $\theta$ik is equal to the critical angle $\theta$ or more and the laser beam is introduced from the introducing surface of the transparent material.

When the light introduced through from the introducing surface repeats the propagation in the transparent material and the light impinges on the introducing surface again, since the light of the critical angle $\theta$ or less impinges, the light leaks. Therefore, when it is desired that the total reflection is more performed in the transparent material (when it is desired to increase m), it is sufficient to reduce such a probability that the light leaks out of the introducing surface. Actually, the beam locus is obtained by a simulation, the light introduced through the transparent material repeats the total reflection at the total reflective surfaces and turning surfaces and propagates, so that the width d of the introducing surface that the number of reflecting times until the light leaks out of the introducing surface increases is determined. Specifically speaking, it is sufficient that the width d of the introducing surface is reduced. Although the width d of the introducing surface is also limited by a beam diameter of the laser beam and a process for the transparent material, it is desirable that d is equal to 0.4 mm or less, preferably, 0.2 mm or less. When it is extremely reduced (it is smaller than 0.1 mm), since a break easily occurs on an interface between the total reflective surfaces and the introducing surface and an interface between the turning surfaces and the introducing surface, it is not preferable.

By selecting the refractive index nt (or wavelength $\lambda$ of the laser beam) of the transparent material, m (the number of reflecting times on the total reflective surfaces) can be adjusted. Specifically speaking, since there is a case where the quality of material of the transparent material is limited in accordance with the use of the transparent material, so that it is preferable to select the wavelength $\lambda$ of the laser beam. The wavelength of the laser beam in which an absorption to the transparent material is little is preferable. When the absorption is large, since there is a possibility that not only a detecting sensitivity of the ununiformity decreases but also the transparent material itself is broken, it is not preferable. The wavelength of the laser beam also exerts an influence onto a resolution of the ununiformity (scratch on the surface or the like). Since the maximum of the resolution of the ununiformity becomes the wavelength $\lambda$ of the laser beam, when it is desired to resolve and detect such a fine defect that the width of a scratch of a glass substrate for an electronic device is equal to 1 $\mu$m or less as an image, the wavelength of the laser beam is set to 1 $\mu$m or less.

When the transparent material has a certain specific form (for example, when the total reflective surfaces are perpendicular to the turning surfaces or the like), since the angle at which the beam impinges on each of the total reflective surfaces and turning surfaces has a predetermined relation with the angle $\theta$1 at which the laser beam first impinges on the total reflective surfaces after completion of the introduction, m (the number of reflecting times on the total reflective surfaces) can be adjusted by properly adjusting the angle $\theta$1. In fact, after the conditions of the transparent material (width d and refractive index nt of the introducing surface) and the conditions of the laser beam (wavelength $\lambda$ and beam diameter $\phi$) are determined, $\theta$1 is adjusted so as to be equal to the reference design value m which permits the transparent material to be filled with light or more, and the laser beam is introduced. Generally, however, there is not a little variation in size (length or the like) of the total reflective surface depending on a difference between processing precisions. When the size of the total reflective surface of the transparent material having the variation is grasped every inspecting sample and the inspection is then performed, it takes an extensive time, so that it is not practicable. Therefore, the laser beam which is introduced through the transparent material can be detected at a high sensitivity and a high speed by fluctuating the incident angle within a range where the total reflection is caused and impinging the beam, so that the inspecting method having a high utility can be realized.

It is preferable that the total reflective surfaces and turning surfaces of the transparent material have such a relation as to cross at right angles to each other. With such a construction, the introduced laser beam easily enters a state where it repeats the total reflection on the total reflective surfaces and turning surfaces and is confined in the transparent material. In face, the inspection for the wide region of the transparent material can be simultaneously executed, so that a high speed inspection can be realized. That is, the reason is that the incident angle of the light is the same on at least the pair of total reflective surfaces on which the introduced laser beam repeats the total reflection and, on at least the pair of turning surfaces as well, the incident angle of the light is the same, so that the light is propagated so as to have a predetermined relation (when the incident angle of the light on the total reflective surface is set to θ, the incident angle of the light on the turning surface is equal to 90°−θ).

In the inspecting region of the transparent material sandwiched by one certain pair of the total reflective surfaces and one certain pair of turning surfaces, the ununiformity in one certain plane in the inspecting region filled with the light due to such a fact that the light is propagated in the transparent material is inspected and, after that, the ununiformity of the inspecting region is inspected by relatively moving the plane of the inspection in the direction in which the inspecting region is filled with the light to the transparent material, so that the inspecting method can be simplified and it is preferable.

Although the concept of the general light confinement of the invention has been explained, when the invention is more specifically embodied, there is provided a method of inspecting an ununiformity of a transparent material by introducing a laser beam through the transparent material, wherein the surface of the transparent material has at least one pair of main surfaces which are parallel to each other, at least one pair of end surfaces which intersect the main surfaces, and chamfer portions sandwiched by the main surfaces and end surfaces, when an optical path in the transparent material is optically uniform, a laser beam is introduced in such a manner that light which propagates in the transparent material and impinges on the main surfaces and the end surfaces of the transparent material is propagated so as to totally reflect and repeat between at least the pair of end surfaces and the laser beam is spread in an inspecting region which is formed by the propagation and is surrounded by the main surfaces, the end surfaces, and the chamfer portions, and when an ununiform portion exists in the optical path of the light introduced and propagated in the transparent material, the light that leaks out of the main surfaces and/or end surfaces is detected, thereby inspecting the ununiformity of the transparent material.

In this instance, the main surfaces, the end surfaces, and each of the chamfer portions correspond to the foregoing total reflective surfaces, the turning surfaces, and the introducing surface. As a representative form having the main surfaces, end surfaces, and chamfer portions, a square (rectangular) plate, a circular plate, an annular plate, or the like can be mentioned. In this case, the introduced laser beam easily enters a state where the laser beam repeats the total reflection on the main surfaces and end surfaces and is (substantially) confined in the transparent material. Actually, since a wide region of the transparent material can be simultaneously inspected and a high speed inspection can be realized, it is preferable. That is, the reason is as follows. Each incident angle of the light on the main surfaces on which the introduced laser beam repeats the total reflection is the same and each incident angle of the light which impinges on the end surfaces is also the same. Since the light is propagated so that those incident angles keep a predetermined relation (when it is assumed that the incident angle of the light which impinges on the main surfaces is set to θ, the incident angle of light which impinges on the end surfaces is equal to 90°−θ), the light confinement is (substantially) satisfied by merely setting so that the incident angle to the main surfaces on which the light first impinges after it introduces through the transparent material is larger than a critical point and the incident angle to the end surfaces is larger than the critical point.

As specific means for introducing the laser beam, the laser beam is introduced so that a singular point that the laser beam geometrically and optically leaks out of the main surfaces and end surfaces does not substantially exist. Further, the laser beam is introduced so that the introduced laser beam is emitted from only the chamfer portions.

It is also preferable that the transparent material serving as an object of the ununiformity inspecting method is made of glass. The quality of material of the transparent material is decided in accordance with various uses. In case of glass, there are advantages that it is hard, a remarkably smooth surface can be obtained by mirror-polishing, light permeability is good, and the like.

When the transparent material is a glass substrate for an electronic device, the ununiformity inspecting method exhibits the effect still more. Since a glass substrate having a surface polished at a high precision is required in association with the realization of high density of a pattern in recent years, the ununiformity inspecting method is effective in inspecting the ununiformity such as fine scratch or striae of the substrate which becomes an adverse influence on a formation or an exposure of the pattern.

When the transparent material is a glass substrate for an information recording medium, the ununiformity inspecting method exhibits the effect more and more. Since the transparent substrate having the surface polished at a high precision is required in association with the realization of high density recording and low flotation of a magnetic head in recent years, the ununiformity inspecting method is effective in inspecting the ununiformity such as a scratch on the substrate surface which becomes an adverse influence onto the realization of high density recording and low flotation of the magnetic head.

Similar to the glass substrate for the electronic device, glass substrate for the information recording medium, or glass substrate for a liquid crystal display, when the material is formed so as to have main surfaces which are parallel to each other and end surfaces which are perpendicular to the main surfaces and so that introduced light repeats the total reflection and is confined in the transparent material, actually, a wide region of the transparent material can be simultaneously inspected, so that the inspection can be performed at a high speed.

An apparatus for inspecting an ununiformity of a transparent material according to the invention is to embody the above inspecting method and is an apparatus for inspecting the ununiformity of the transparent material by introducing a laser beam through the transparent material, comprising: illuminating means (irradiating means) for introducing a laser beam through the transparent material; and detecting means for detecting light which leaks out of the transparent material, wherein the transparent material has an introducing surface for introducing the laser beam through the transparent material and at least two pairs of surfaces on which the introduced laser beam repeats a total reflection and which face each other, and the illuminating means is arranged so that a laser beam emitted from the illuminating means is introduced from the introducing surface, when an optical path in the transparent material is optically uniform, light which propagates in the transparent material and impinges on the surfaces of the transparent material is propagated so as to totally reflect and repeat at least one pair of surfaces among the above-mentioned surfaces, and the laser beam is spread in an inspecting region which is formed by the propagation and is surrounded by at least the two pairs of surfaces. With such a construction, the inspection of the ununiformity of the transparent material can be automatically executed, an inspecting time can be reduced, and a reliability of the inspection can be improved.

In the inspecting apparatus, it is preferable that angle adjusting means for changing an incident angle of the laser beam to the transparent material is provided for the illuminating means. The angle adjusting means adjusts the incident angle so that the laser beam introduced through the transparent material repeats the total reflection on the surface of the transparent material and the light is confined and is also used when the incident angle is fluctuated within a range where the total reflection occurs in order to absorb a variation in size due to a difference between processing precisions of the transparent material.

As representative angle adjusting means, a mirror can be mentioned. The mirror is arranged between the illuminating means (for example, a laser) and the transparent material and adjusts the incident angle for the transparent material. In addition to the mirror, it is also sufficient that angle adjusting means for changing an angle of the illuminating means to the transparent material is provided for the illuminating means itself or angle adjusting means is provided for a folder for holding the transparent material. Means for adjusting and fluctuating the incident angle by using an acousto-optical effect of an ultrasonic beam such as an acousto-optical polariscope can be also used.

In the inspecting apparatus, it is preferable to provide moving (scanning) means for moving (scanning) an incident position of the laser beam on the transparent material It is because the whole region of the transparent material can be exhaustively and automatically inspected. For example, illuminating means such as a laser and angle adjusting means such as a mirror are mounted on the same table. By attaching a driving apparatus to the table, consequently, they can be sequentially moved along one side of the transparent material or by attaching a driving apparatus to the folder for holding the transparent material, the folder can be moved.

In the inspecting apparatus, it is preferable that the transparent material and detecting means are integratedly and relatively moved for the illuminating means. When a detecting region of the detecting means is larger than the inspecting region, the transparent material is relatively moved for the illuminating means, so that the inspection of the ununiformity can be performed. However, since the inspecting region is generally larger than the detecting region of the detecting means, the transparent material and detecting means are integratedly and relatively moved for the illuminating means. When they are relatively moved, it is also possible that the illuminating means, namely, an illuminating optical system such as a laser is fixed and the transparent material and/or detecting means are moved by using the driving apparatus or the like, or the transparent material and/or detecting means are fixed and the illuminating optical system such as a laser is moved.

In the inspecting apparatus, it is preferable that the detecting means has an image pickup camera having an image pickup device (CCD or the like) and a lens for forming, as an image onto the image pickup camera, the light which leaks out of the transparent material, and the image pickup camera and/or lens are relatively moved in the depth direction for the transparent material. By relatively moving the image pickup camera and/or lens in the depth direction for the transparent material, a focusing of the image pickup camera can be performed, so that accurate information of the ununiformity (scratch on the surface, internal striae, bubbles, or the like) in the thickness direction of the transparent material can be obtained. For example, the detecting means such as image pickup camera and lens are fixed and the transparent material, laser, and mirror are integratedly moved in the depth direction of the detecting means. On the contrary, it is also possible that the transparent material, laser, and mirror are fixed and the detecting means such as image pickup camera and lens are moved.

In the inspecting apparatus, it is desirable to provide discriminating means for discriminating the presence or absence, kind, and size of the ununiformity of the transparent material on the basis of the information detected by the detecting means.

With respect to the presence or absence, kind (scratch or crack on the surface portion, striae or foreign matter in the inside, or the like), size (area, length, width, depth, region, or the like) of the ununiformity which previously exists in the transparent material, (image) information of the light which leaks out of the surface, a relation (information) between (a light quantity of the leak light, luminance, intensity distribution, depth from the surface, or the like) are accumulated in a computer or the like and (image) information of the light detected by the inspection is compared with the accumulated information, so that the kind and size of the ununiformity of the transparent material can be discriminated. As mentioned above, by discriminating the presence or absence, kind, and size of the ununiformity of the transparent material, a desired transparent material can be extracted. Therefore, for example, a glass substrate having an ununiformity that has an influence at the time of a formation of a pattern or an exposure for a transferring object can be eliminated before the following process after completion of the inspection or can be returned to a re-polishing process, so that the productivity can be improved.

In the ununiformity inspecting apparatus, it is preferable that as for the information of the detected light, when the light detected by the CCD is converted to an SIN ratio ($10 \cdot \log_{10}(S/N)$) for normalized exposing time of the CCD and is processed, the S/N ratio ($10 \cdot \log_{10}(S/N)$) is equal to 4.8 dB or more so long as the normalized exposing time is equal to 0.025 or more. In this instance, the normalized exposing time is defined as (exposing time of the CCD)/(maximum exposing time of the CCD until a signal of a background reaches (20000/4095)×100 electrons). The foregoing normalized exposing time can be freely set due to measuring conditions or inspecting apparatus.

The reason is that when the S/N ratio is equal to 4.8 dB or more (an amount of the signal for the background is equal to a value that is three times as high as that of noises), the value is an image processing possible level which is generally known, so that the presence or absence, kind, and size of the ununiformity of the transparent material can be accurately discriminated.

A method of selecting a transparent substrate according to the invention is characterized by comprising the steps of: preparing a transparent substrate having an introducing surface to which a laser beam is introduced, at least one pair of main surfaces on which the introduced laser beam repeats a total reflection and which face each other, and at least one pair of end surfaces provided so as to face each other in the progressing direction of light; introducing the laser beam from the introducing surface in such a manner that when an optical path in the transparent substrate is optically uniform, light which propagates in the transparent material and impinges on the main surfaces and the end surfaces of the transparent material is propagated so as to totally reflect and repeat between at least the pair of end surfaces and the laser beam is spread in an inspecting region which is formed by the propagation and is surrounded by the main surfaces and the end surfaces; detecting light which leaks out of the main surfaces and/or end surfaces without being totally reflected; and comparing the detected Information with information which has previously been stored and which corresponds to the presence or absence, kind, and size of an ununiformity existing in the transparent substrate, thereby selecting the transparent substrate.

BEST MODE FOR CARRYING OUT THE INVENTION

Embodiments of the invention will now be described hereinbelow by using the drawings. FIG. 1 is a schematic constructional diagram showing an embodiment of an apparatus for inspecting an ununiformity of a transparent material according to the invention.

Figure 2:
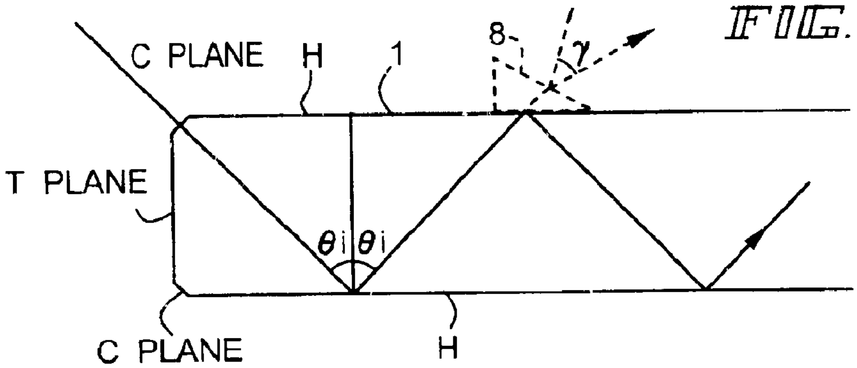
FIG. 2 is a side elevation view in which a part of the transparent substrate in FIG. 1 is enlarged.

In FIG. 1, reference numeral 1 denotes a transparent substrate made of glass such as optical glass serving as an inspecting object. As shown in FIG. 2, the transparent substrate 1 has parallel planes which face each other and are constructed by main surfaces (surface and rear surface) H and end surfaces (T planes and C planes as chamfer portions). Every plane is mirror-polished and, after that, it is cleaned. The main surfaces (surface and rear surface) have a role that the laser beam introduced through the transparent substrate repeats a total reflection and propagates and have a function as a total reflective surface. The end surfaces (T planes) are arranged so as to face each other in the progressing direction of the light, allow the light which repeated the total reflection on the main surfaces and propagated to repeat between mirror surfaces which face each other, and have a function as a turning surface for turning the introduced and propagated light. The C planes are planes sandwiched by the main surfaces and end surfaces (T planes). Generally, in the C plane, since a fine scratch on the surface hardly becomes a problem, the plane is not regarded as an object of the inspecting region. In the invention, it has a function as an introducing surface for introducing the laser beam.

In this instance, every surface of the main surfaces (surface and rear surface) as total reflective surfaces, end surfaces (T planes) serving as turning surfaces, and C planes serving as introducing surfaces is mirror polished. Particularly, such a fact that the introducing surfaces are mirror polished has a sense in the light confinement of the invention. That is, by mirror-polishing the introducing surfaces, the introduced laser beam propagates as almost parallel light without substantially being scattered, so that it is possible to adjust almost all of the light which impinges on the main surfaces and end surfaces so as to be totally reflected. When the introducing surfaces are not mirror-polished, the light is scattered on the introducing surfaces, the light of a plurality of directions propagates, and every beam locus cannot be expected, so that the light confinement of the invention is not satisfied. Although explanation is made with respect to such a fact that the introducing surfaces are mirror-polished, so long as the laser beam can be introduced so that all of the laser beams are totally reflected on the main surfaces on which the laser beam that is introduced into the substrate at least first impinges, it is unnecessary to mirror-polish. For example, by coating matching oil or the like having the same refractive index as that of the substrate in order to form a pseudo mirror surface onto the introducing surfaces as mirror surfaces, the light confinement of the invention is also realized.

Figure 3:
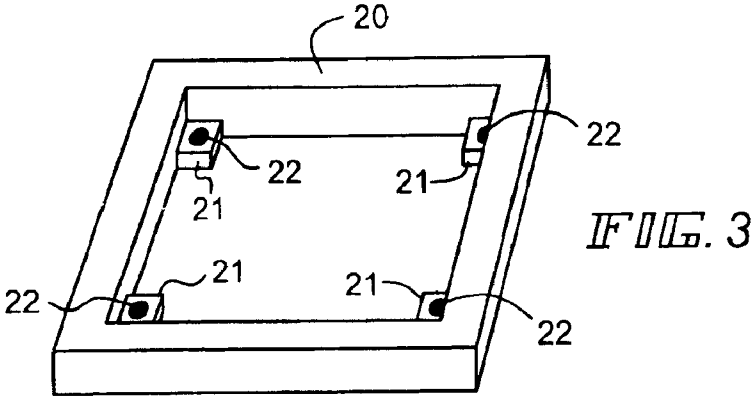
FIG. 3 is a perspective view showing an example of a folder for holding the transparent substrate.

In order not to impede the total reflection on the surface and to easily execute the inspection of the leak light, the transparent substrate 1 is horizontally held by a folder so as to reduce a contact portion as little as possible. FIG. 3 shows an example of the folder of the transparent substrate 1. A folder 20 has a rectangular framing form for holding the transparent substrate 1. Receiving portions 21 for supporting corner portions of the bottom surface of the transparent substrate 1 are formed at four corners on the inner side of the bottom of the folder 20. Spheres 22 for supporting the transparent substrate 1 at dots so as to be come into contact with it are placed.

Illuminating means for introducing the laser beam to inspect an ununiformity from the side surface of the transparent substrate 1 is provided for the transparent substrate 1. The illuminating means has: a laser 2 as a light source for emitting an illuminating light; and mirrors 31 and 32 for allowing the laser beam to illuminate at predetermined position and angle of the C plane. The laser 2 and mirrors 31 and 32 are placed on a table 5 on which a driving apparatus 4 for moving the laser beam in parallel with the direction of a side 1*a* of the transparent substrate 1. In the embodiment, in order to relatively move the laser 2 and mirrors 31 and 32 for the transparent substrate 1 and detecting means, the transparent substrate 1 and detecting means are fixed and the laser 2 and mirrors 31 and 32 can be integratedly moved by the driving apparatus 4. (It is also sufficient that the driving apparatus is attached to the transparent substrate 1 and detecting means, the laser 2 and mirrors 31 and 32 are fixed, so that the transparent substrate 1 and detecting means can be integratedly moved.) In order to detect the ununiformity in the thickness direction of the transparent substrate 1 by executing a focusing of a CCD when the laser beam is introduced, the table (not shown) on which the laser 2 and mirrors 31 and 32 are placed can be moved in the directions of X, Y, and Z. The mirrors 31 and 32 are used for a fine adjustment of an angle or the like. It is also sufficient to directly irradiate the laser beam onto the substrate 1 from the laser 2 without using the mirrors 31 and 32. Incident angle adjusting means can be also provided so as to enable the laser beam introduced through the transparent substrate 1 to impinge by fluctuating the incident angle in a range where the laser beam causes the total reflection. As incident angle adjusting means, means having a mechanism for automatically adjusting angles of the mirrors 31 and 32 by a control of a computer or the like or means such as an acousto-optical polariscope for allowing the incident angle by using an acousto-optical effect of an ultrasonic beam can be also used.

Detecting means for detecting the laser beam which leaks out of the transparent substrate 1 is provided above the transparent substrate 1. The detecting means has a CCD 6 and a lens system (image forming optical system) 7 for forming, as an image onto the CCD 6, the light leaked out of the transparent substrate 1. An optical sensor for detecting the light leaked out of the transparent substrata 1 is not limited to the CCD but a photo-multiplier or the like can be also used. When a flexible laser beam is used as illuminating light, the leak light from the substrate 1 is detected by eye observation and the detecting means can be also omitted. When the CCD is used as detecting means, there are a CCD of a full frame system having a mechanical shutter function and one of an interline system in which the mechanical shutter is not needed. In consideration of a durability, the CCD of the interline system is preferable. In order to reduce noises, it is also desirable that the CCD has a forced radiating fan or a thermoelectric cooling function.

An image processing apparatus 12 constructed by a computer or the like to process a detected image is connected to the CCD 6 through an A/D converter 11 for converting a detected analog signal into a digital signal.

The image processing apparatus 12 has a function for analyzing an image signal from the CCD 6 and displaying a form pattern, a light quantity, an intensity distribution, or the like of the leak light due to the ununiformity and a discriminating unit for discriminating the presence or absence, kind (scratch or crack on the surface portion, striae, foreign matter in the inside, or the like), size (area, length, width, depth, region, or the like) of the ununiformity of the transparent substrate 1. As information (form pattern, light quantity, luminance, intensity distribution, depth from the surface, or the like of the leak light) of the leak light which corresponds to the kind or size of the ununiformity existing in the transparent substrate, measurement values (basic data) and the like previously obtained by measurements have been inputted to a storage unit of the image processing apparatus 12.

A specific inspecting method executed by using the inspecting apparatus in FIG. 1 will now be described. As an inspecting object, a glass substrate for a photo mask, whose size is 152.4×152.4×6.35 mm and in which a width of the C plane is 0.4 mm is inspected. As shown in FIG. 2, the laser beam is impinged from the C plane of the glass substrate so that an incident angle θi to the main surface on which the laser beam first impinges after it introduces through the glass substrate is larger than a critical angle θc and an incident angle (90°−θi) to the end surface of the glass substrate is larger than the critical angle θc. Since a refractive index of the glass substrate is 1.47 and the critical angle θc is about 42.9°, the incident angle θi is set to 44.1°. That is, the method of introducing is characterized with respect to a point that the laser beam is introduced so that a singular point that the laser beam (geometrically and optically) leaks does not exist on the main surfaces and end surfaces of the glass substrate and the introduced laser beam is emitted only from the C planes. As a laser, an He—Ne laser is used and a laser beam in which a beam diameter is 0.5 mm, a spread angle of the beam is 1 mrad, a laser power is 0.5 mW, and a wavelength is 543 nm is irradiated.

Since the substrate which is used this time has a form in which all of the main surfaces as total reflective surfaces and the end surfaces as turning surfaces have such a relation as to cross at right angles to each other, the incident angles of the light which impinges on the main surfaces are the same, the incident angles of the light which impinges on the end surfaces are the same, and the light propagates so that those angles have a predetermined relation (when the incident angle of the light which impinges on the main surface is set to θi, the incident angle of the light which impinges on the end surfaces is equal to 90°−θi). Therefore, by merely setting so that the incident angle θi to the main surface on which the light first impinges after it introduces through the glass substrate and the incident angle 90°−θi to the end surface are larger than the critical angle θc, the light confinement is realized. In case of a normal form (for example, a form in which the main surfaces and end surfaces do not have such a relation as to cross at right angles to each other, it becomes complicated slightly. In this instance, when it is assumed that the refractive index of the glass substrate for a wavelength λ of the laser beam which is introduced is set to nt, a refractive index ni of an external medium (air) which is come into contact with the glass substrate is set to 1, an angle at which the light impinges on the main surfaces and end surfaces of the glass substrate is θik (k denotes a position where the laser beam impinges on the main surfaces and end surfaces after it is introduced through the glass substrate and the incident positions k are sequentially set as k=1, 2, . . . ), the light confinement is not realized unless the laser beam is introduced so that each θik is equal to the critical angle θ shown by sin θ=ni/nt or more. As mentioned above, the case where the main surfaces and end surfaces have such a relation as to cross at right angles to each other is more effective against the light confinement.

As shown in FIG. 1, the laser beam introduced through the transparent substrate (glass substrate) 1 by the illuminating means repeats the total reflection on the main surfaces and end surfaces of the substrate 1 and enters a state where the light is almost confined in the substrate 1. The state where the light is almost confined means that the introduced laser beam propagates in the transparent substrate and repeats the total reflection and continues to propagate in the transparent substrate until the light impinges on the chamfer portion serving as an introducing surface, namely, so long as it impinges on the main surfaces and end surfaces. Therefore, the laser beam incident in the Y direction is scanned everywhere so as to be spread in a region (measuring region) of a cross section (YZ cross section) obtained by cutting the substrate 1 in the Y direction by the propagation due to the total reflection of the light itself.

As mentioned above, the laser beam introduced through the glass substrate repeats the total reflection on the main surfaces and end surfaces of the glass substrate and enters the state in which the beam is almost confined in the glass substrate. However, when there is a scratch or the like on the glass surface due to a mixture of a foreign matter upon polishing, the total reflecting conditions are not satisfied, so that the light leaks out of a portion of the scratch. With respect to a defect of the glass in which a transmission is the same but a refractive index alone is different, which fact is peculiar to the striae of the glass as well, the light is out of an inherent orbit (optical path) at a portion where the refractive index is different and leaks to the outside of the substrate 1 without being totally reflected on the main surfaces and end surfaces. The leak light is detected by the detecting means.

Due to the light irradiation in the above one cross section, the inspection of one line as observed from the main surface side can be executed. The inspecting process is executed by moving the table 5 in the direction (X direction) of one side 1*a* of the substrate 1 by the driving means 4, so that the ununiformity of the whole region of the substrate 1 can be inspected. That is, it is a method of inspecting an ununiformity in such a manner that in an inspecting region of a substrate sandwiched by main surfaces as one certain pair of total reflective surfaces and end surfaces as one certain pair of turning surfaces of the substrate, an ununiformity (defect) on one certain plane in the inspecting region filled with light by propagating the light in the substrate is inspected and, after that, the inspected plane is relatively moved in the direction which permits the inspecting region to be filled with the light for the substrate.

Figure 4:
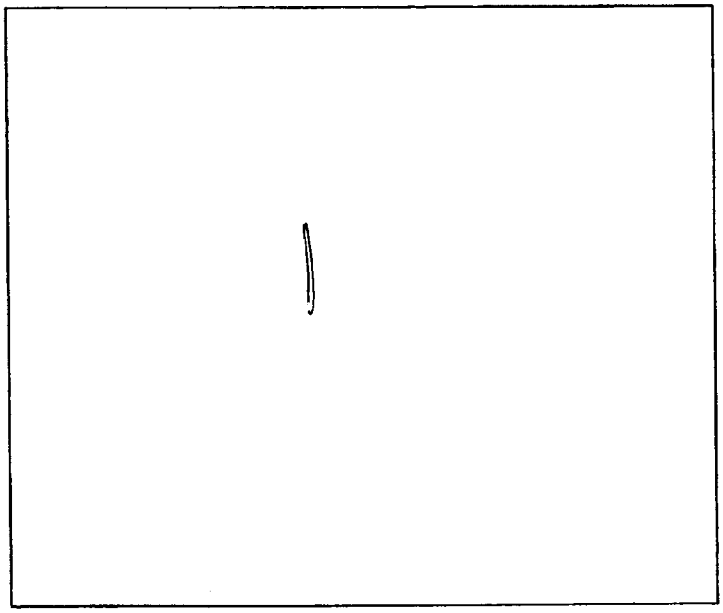
FIG. 4 is an image of a scratch on the surface of a glass substrate detected by the inspecting apparatus in FIG. 1.
Figure 5:
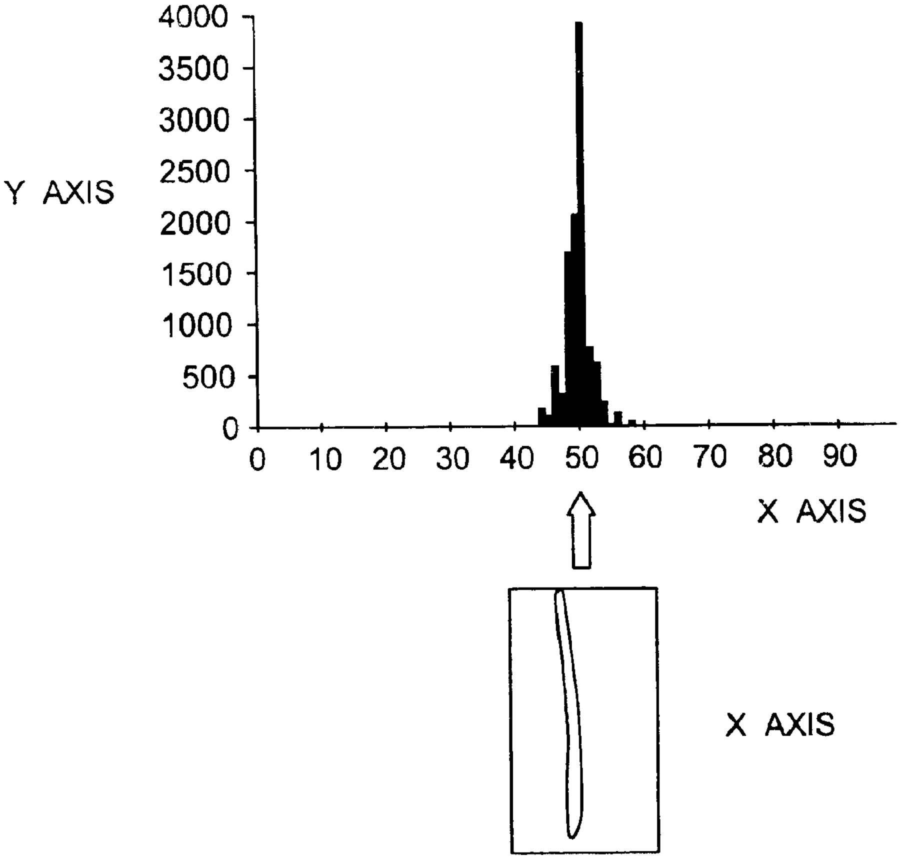
FIG. 5 is a diagram showing a light intensity distribution in the width direction of the scratch obtained by light information of the image of FIG. 4 by an image process.

A result detected by the inspecting apparatus is shown in FIGS. 4 and 5. FIG. 4 shows an image of a scratch on the surface of the glass substrate detected by the CCD 6. FIG. 5 is a graph obtained by performing an image process to information of the light detected by the CCD on one certain side in the width direction of the scratch by a computer via an A/D converter (analog-digital converter). The CCD used at that time is a CCD of the interline system (having no mechanical shutter) in which a thermoelectric cooling function is mounted and in which the number of elements is 1300×1030, a detecting area is 8.71×6.90 mm, and a saturation amount of the CCD is 20000 electrons. As for the measuring conditions, an exposing time of the CCD is set to 200 msec.

An X axis of FIG. 5 denotes a coordinate in the width direction of the scratch. A Y axis denotes an intensity of the detected light. A unit of a scale of the X axis is a pixel. In the inspecting apparatus, since an objective lens of ×50 (50 times) and an image forming lens of ×0.45 (0.45 times) are used, one pixel is 6.7 [$\mu$m]/(50×0.45), namely, it corresponds to about 0.3 $\mu$m. (6.7 $\mu$m indicates a size of one pixel of the CCD.) The light intensity is resolved to 12 bits (4096:1) and one scale denotes (20000/4095)·Y(Y: scale) electrons. As will be obviously from FIG. 5, the intensity of the light leaked out of the scratch is (20000/4095)×4095=20000 electrons as a peak value that exceeds a allowance value of the CCD and the intensity of light in a region other than the scratch is equal to 0. As mentioned above, in an image which is detected by the detecting means, the ununiform portion in which the scratch or the like exists is brightly seen in a linear or a dot form in a black background. The ununiform portion such as a scratch can be clearly discriminated from the obtained image. In this instance, when the propagation due to the total reflection in the glass substrate is considered, there is no factor that the light in the substrate is weaken during the propagation except for a very slight absorption in the uniform portion, so that the light continues to propagate in the glass substrate. Therefore, almost all of the irradiated light concentrate on the ununiform portion as a result. The ununiform portion sharply appears at a very clear contrast. Therefore, a minute scratch or the like can be detected at a high sensibility.

Figure 6:
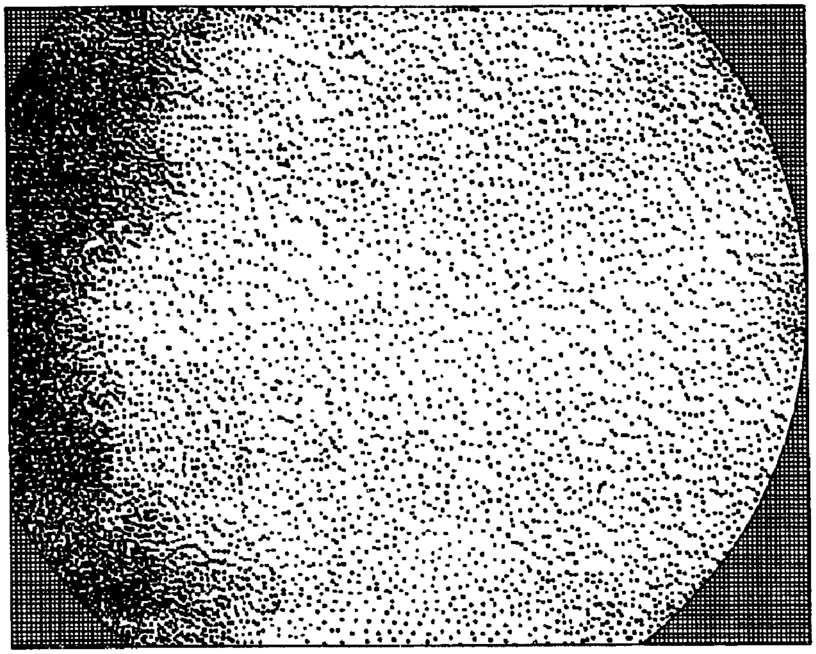
FIG. 6 is an image when the scratch of FIG. 4 is observed by an optical microscope (reflection·bright field)
Figure 7:
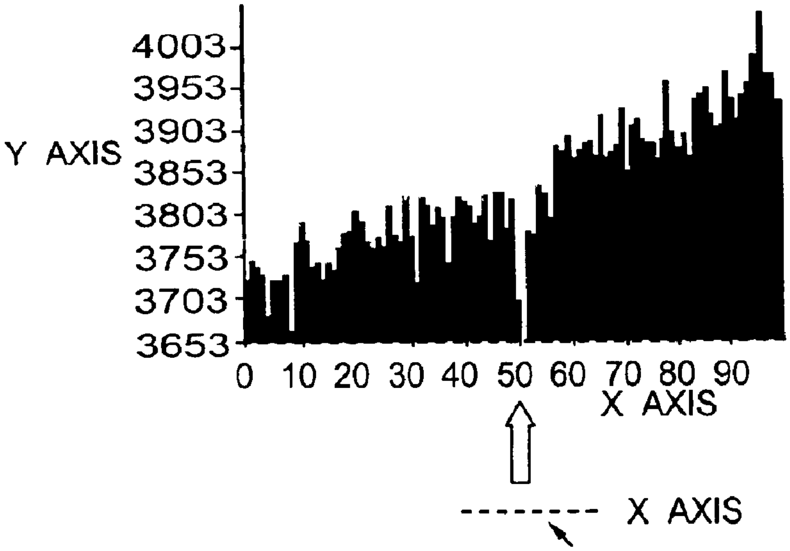
FIG. 7 is a diagram showing a light intensity distribution in the width direction of the scratch obtained from light information of the image of FIG. 6 by the image process.

FIG. 6 shows an image of a scratch similar to that of FIG. 4 observed by an optical microscope (reflection·bright field). FIG. 7 is a graph showing the image to which the image process similar to that in FIG. 5 was performed. As will be understood from FIGS. 6 and 7, signals of the scratch are buried by signals of the background and the scratch cannot be detected by the method. When the scratches of FIGS. 4 and 6 are observed by an atomic force microscope (AFM), each of them is confirmed as a scratch in which the width is 0.13 $\mu$m and the depth is 0.0013 $\mu$m.

In the above embodiment, when it is desired to confirm the incident angle θi of the laser beam to the transparent substrate 1, for example, as shown in FIG. 2, so long as an wedged optical member 8 is arranged on the substrate surface via matching oil or the like, the incident angle θi can be obtained from a refractive index γ of light which is emitted from the optical member 8 or an apex angle of the optical member 8. When something like the optical member 8 is used as an entrance window to introduce the inspecting light into the substrate, the light can be also introduced from portions other than the chamfer portions (C planes) of the substrate.

Figure 8:
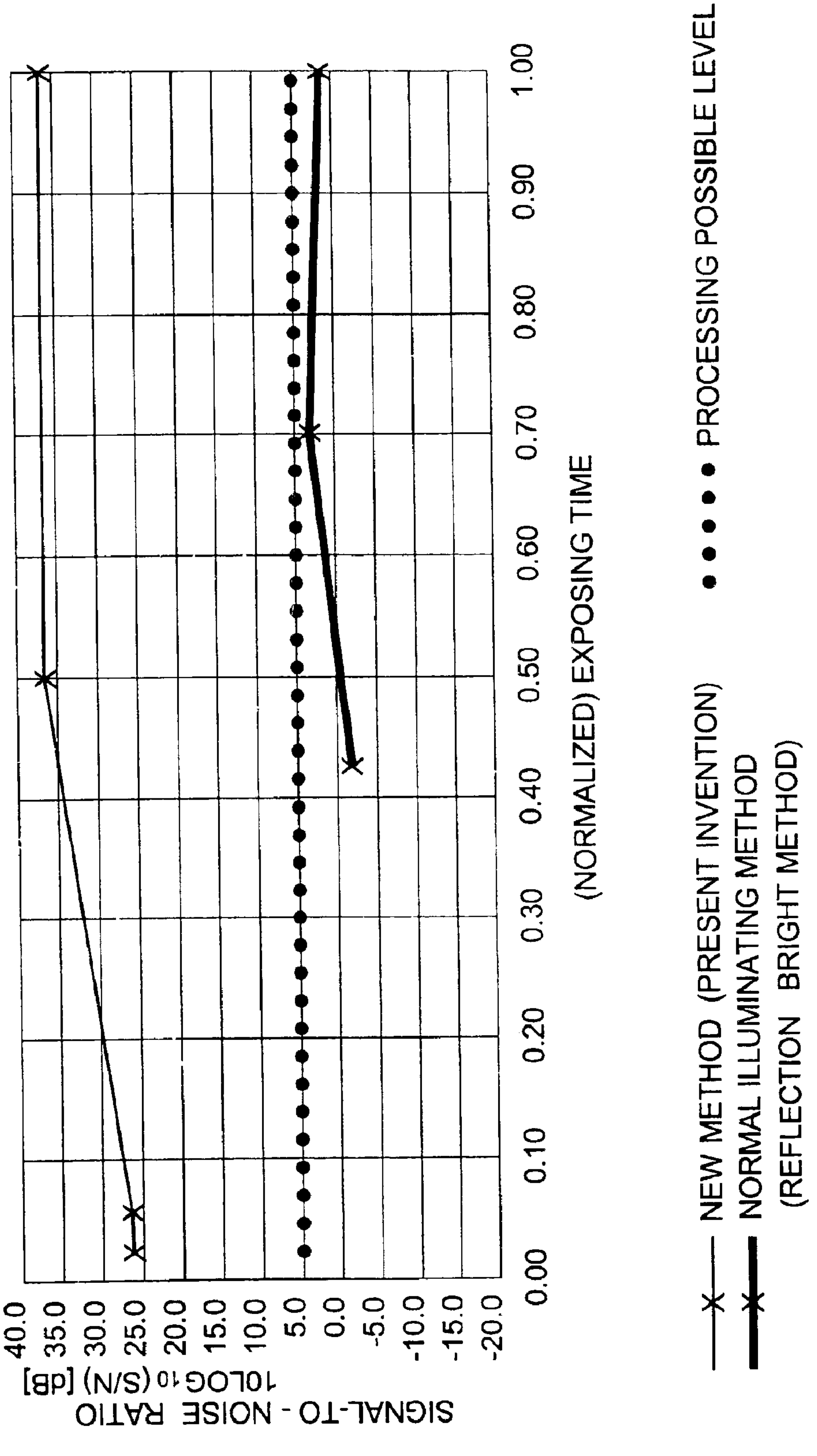
FIG. 8 is a graph in which a detection sensibility of the method according to the invention is compared with that of a conventional method and which shows a relation between a signal-to-noise ratio (hereinbelow, referred to as an S/N ratio) and normalized exposing time.

FIG. 8 shows a relation between an S/N ratio and a normalized exposing time when an arbitrary scratch is observed and the image process similar to the above is performed in order to clarify a difference between a case where the ununiformity is detected by the optical microscope in a conventional normal illumination and a case where the ununiformity is detected by the inspecting method of the present invention. In this instance, the normalized exposing time is defined as (exposing time of the CCD)/(maximum exposing time of the CCD until the signals in the background reach (20000/4095)×100 electrons) and the S/N ratio is set to $10\cdot\log_{10}(S/N)$. As will be obviously understood from FIG. 8, in the inspecting method in the conventional normal illumination, even when the normalized exposing time is extended, an maximum is at most 3 dB. In the inspecting method of the present invention, the S/N ratio exceeds 30 dB as a result. In the inspecting method of the invention, the SIN ratio is limited up to 36 dB as maximum. It is because the saturation amount of the CCD camera is limited. It is considered that an extremely high S/N ratio exceeding 36 dB is actually obtained. (It is considered that the reason why the S/N ratio in the normal illumination indicates a minus value is that the signal of the scratch is buried by noises.) According to the inspecting method of the present invention, therefore, the S/N ratio exceeds 4.8 dB (the signal for the background is equal to an amount that is three times as much as that of noises) which is generally known as an image processing possible level by far, so that the presence or absence, kind, and size of the ununiformity in the transparent material can be accurately discriminated.

In the above embodiment, the incident angle θi is set to 44.1°. The optimum incident angle at which the total reflection is repeated more can be easily selected by simulations shown as follows. The results obtained by simulating a situation in which the light propagates in the transparent substrate will now be explained hereinbelow.

Figures 9, 10:
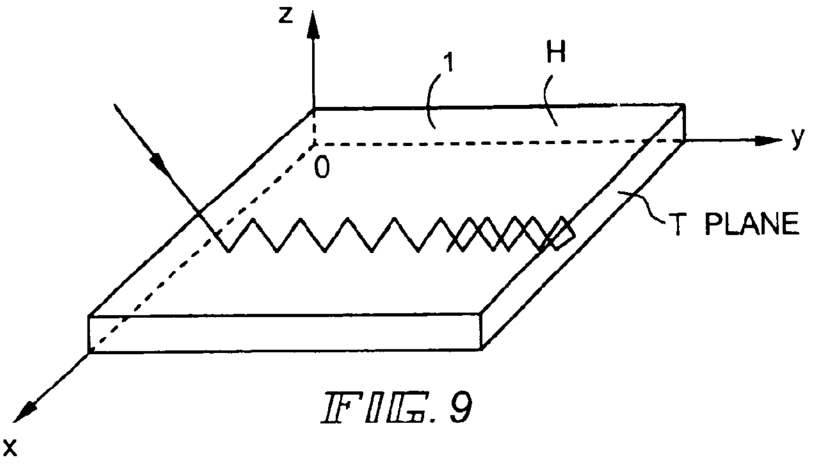
FIG. 9 is a perspective view for explaining a simulation for obtaining a beam locus in the transparent substrate when a laser beam is introduced into the transparent substrate along one side.
FIG. 10 is a diagram showing an example of a result according to the simulation of FIG. 9.

First, a calculation result when the light is propagated along one side (in the y axial direction) of the transparent substrate 1 as shown in FIG. 9 will now be described. In the simulations, the dimension of the transparent substrate 1 is 152.4×152.4×6.35 mm that is the same as that of the glass substrate for the photo mask in the foregoing embodiment. The width of C plane is set to 0.4 mm. The refractive index of the transparent substrate 1 is set to 1.47 that is a refractive index of quartz glass and the refractive index around the transparent substrate 1 is set to 1.00 that is a refractive index of air. A vector (unit vector) indicative of the direction of the beam which impinges on the C plane (which forms an angle of 45° against the main surface and T plane) obtained by chamfering the transparent substrate 1 is set to (0.0000000, 0.6864532, −0.7271740). FIG. 10 shows results of the simulations.

In FIG. 10, the incident angle is the incident angle to the surface (main surface) on which the beam first impinges after it enters the substrate 1. The incident angle is changed every 0.05 degree of angle. A z coordinate upon emitting indicates a z coordinates when the beam is emitted from the transparent substrate 1 and the bottom surface of the substrate 1 is set to z=0.

Figure 11:
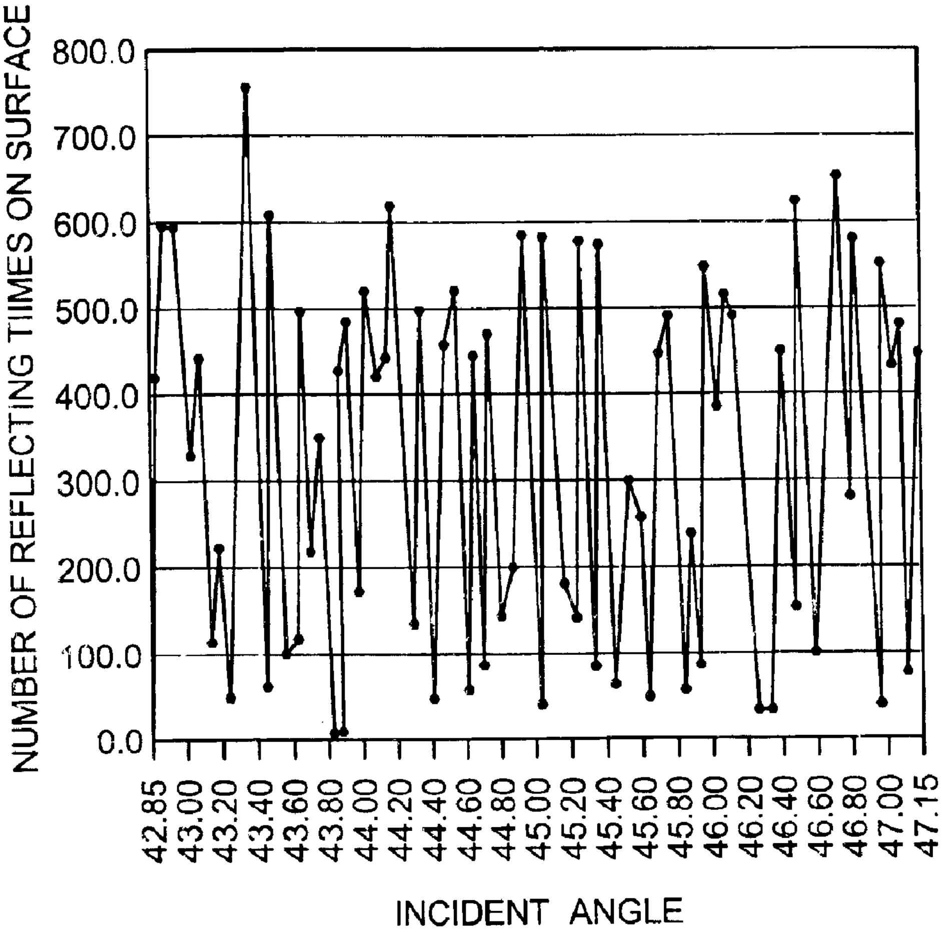
FIG. 11 is a graph showing a relation between an incident angle to the transparent substrate and the number of reflecting times on surfaces in FIG. 10.

FIG. 11 is a graph showing the number of reflecting times on the surfaces at respective incident angles. As will be understood from FIG. 11, it is sufficient that the incident angle at which the number of reflecting times on the surfaces increases is selected in accordance with the form or the like of the transparent substrate. It is also sufficient that the incident angle of the light which is introduced is fluctuated.

Figure 12:
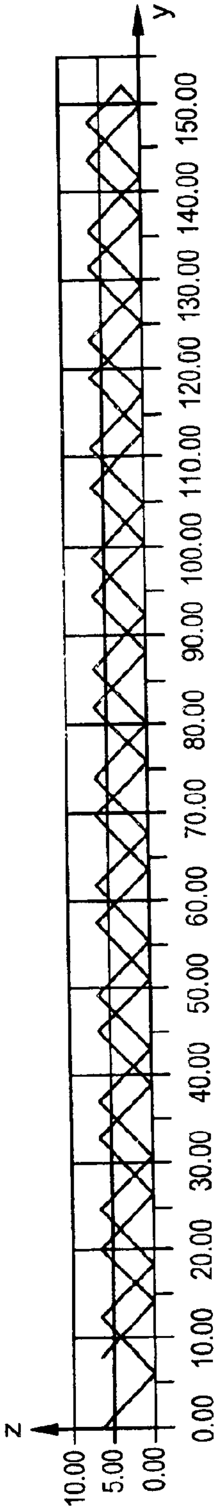
FIG. 12 shows graphs of the beam loci showing states of the propagation of the light in the transparent substrate obtained by the simulation of FIG. 9.
Figure 12:
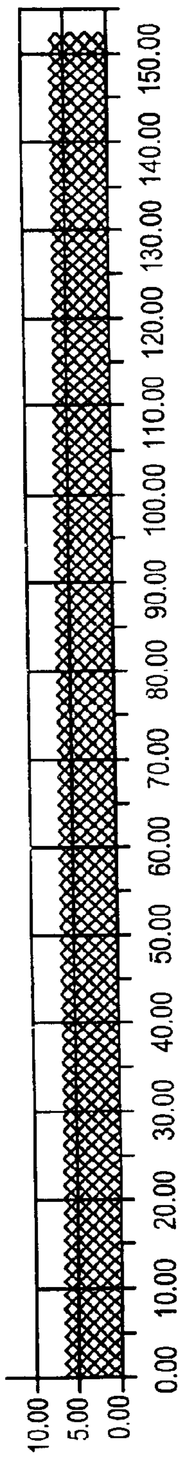
Figure 12:

FIG. 12 shows states of the propagation of the light in the substrate in case of the incident angle of 43.35°. FIGS. 12(1), (2), and (3) show states in which the number of reflecting times on the surfaces are set to 50, 250, and 661 times (upon emitting), respectively. In this simulation, in order to simplify the calculation, the propagation is performed in the only region in the cross section of one plane (yz plane). As shown in FIG. 12, it will be understood that the light beam repeats the total reflection and propagates so as to fill the region. In a manner similar to the simulation, when the parallel light is introduced in the one side (y direction) of the transparent substrate, in order to impinge the illuminating light on the whole region of the transparent substrate, it is sufficient that the light is scanned along another side (x direction) by using a mirror or the like or the light spread in a slit shape in the x direction is introduced from the C plane.

Figure 13:
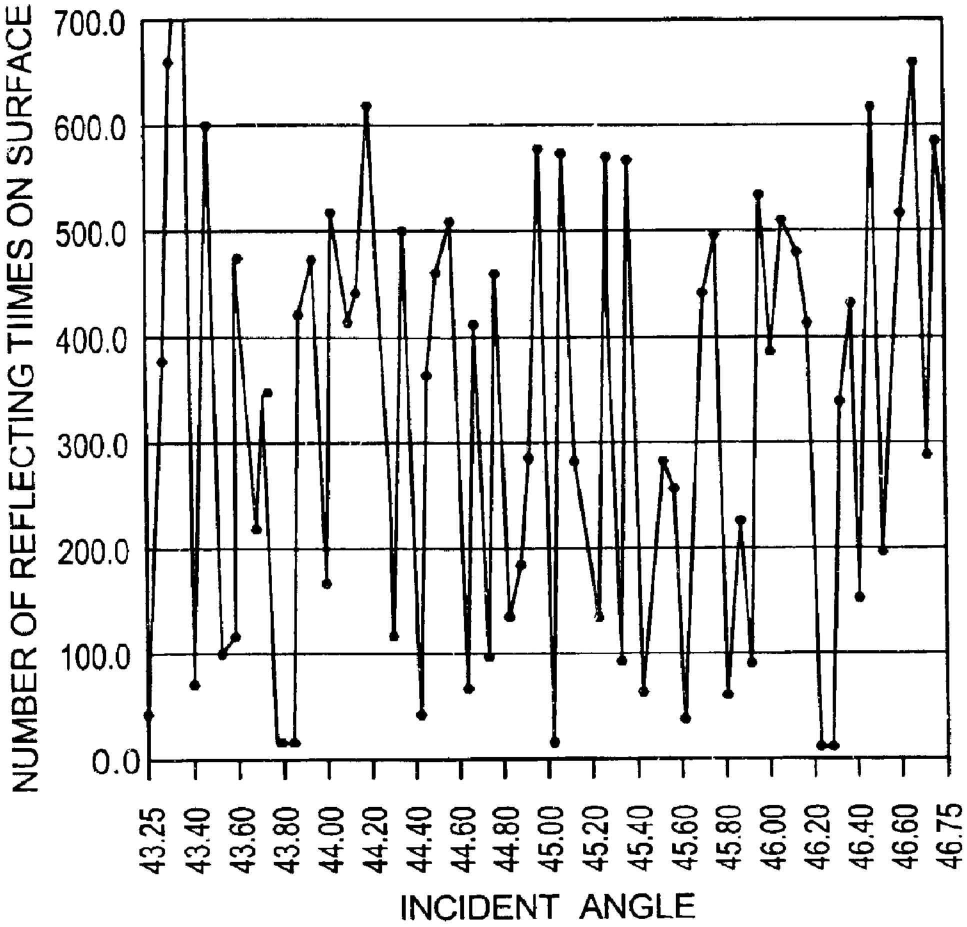
FIG. 13 is a graph showing a relation between the incident angle to the transparent substrate and the number of reflecting times on the surfaces in another example of the simulation of FIG. 9.
Figure 14:
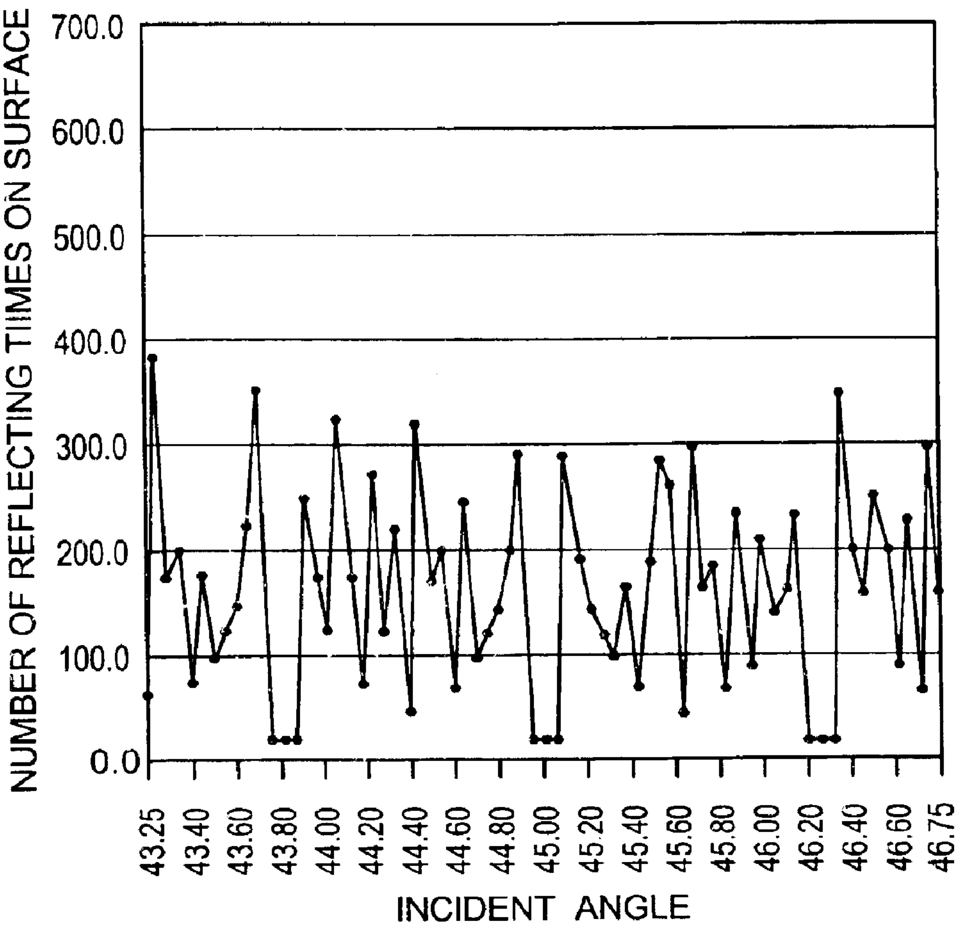
FIG. 14 is a graph showing the relation between the incident angle to the transparent substrate and the number of reflecting times on surfaces in the other example of the simulation of FIG. 9.
Figure 15:
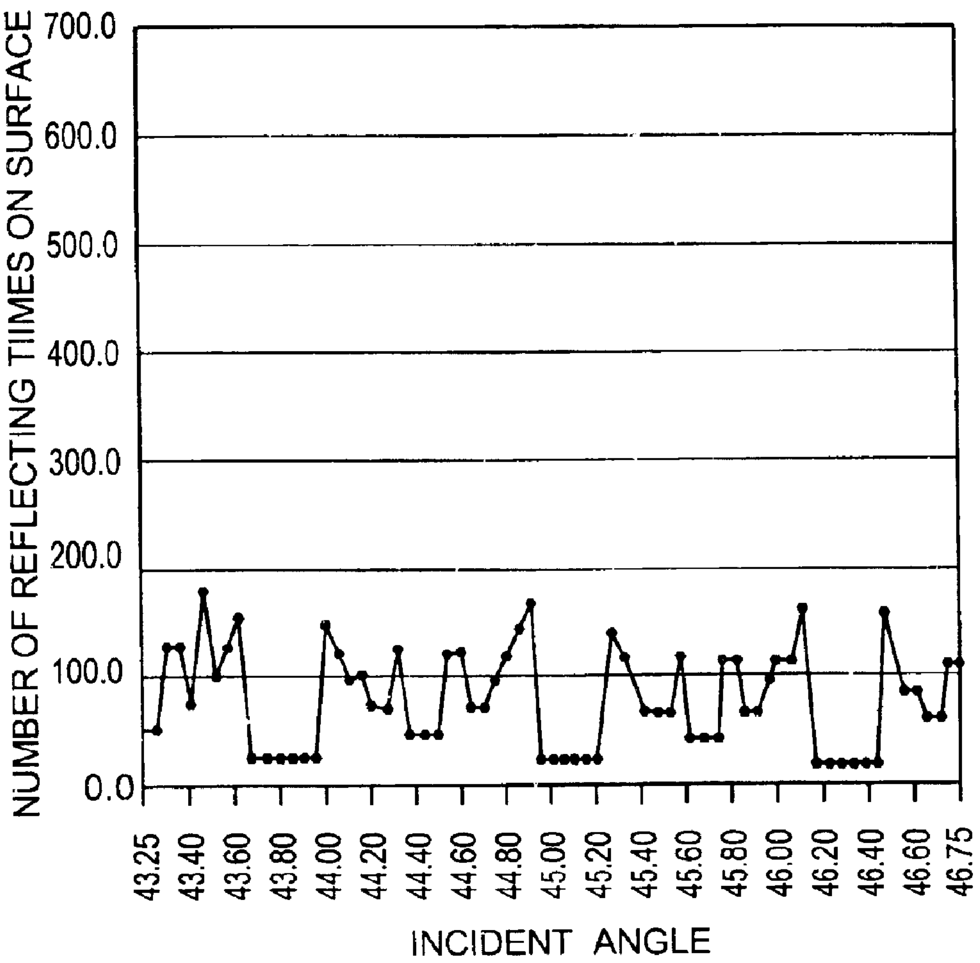
FIG. 15 is a graph showing the relation between the incident angle to the transparent substrate and the number of reflecting times on surfaces in the other example of the simulation of FIG. 9.

The simulation results when the width of C plane, refractive index of the glass substrate (corresponding to the wavelength of the laser beam) in the simulation of FIG. 9 are changed are shown in FIGS. 13, 14, and 15. The simulation is executed under the conditions similar to those of the simulation executed in FIG. 9 other than a fact that the refractive index of the glass substrate is set to 1.46 (corresponding to the wavelength of the laser beam that is equal to 543 nm) and the width of C plane is changed to 0.2 mm (FIG. 18), 0.4 mm (FIG. 14), and 0.8 mm (FIG. 15).

As will be understood from FIGS. 13 to 15, as the width of C plane increases, the number of reflecting times on the surfaces decreases. The reason is as follows. When the laser beam introduced from the C plane propagates in the transparent substrate and again impinges on the C plane, the beam leaks without being totally reflected because the light incident to the C plane is impinged at an angle that is smaller than the critical angle θ. Consequently, a probability that the light propagated in the transparent substrate impinges on the C plane is raised by increasing the width of C plane. Therefore, in order to increase the number of reflecting times on the surfaces in the transparent substrate, it is sufficient to reduce the width of C plane. In case of the glass substrate (152.4×152.4×6.35 mm) for the photo mask used at this time, since the transparent substrate is sufficiently filled with the light so long as the number of reflecting times on the surfaces is about 300 times, it is preferable that the width of C plane is equal to 0.4 mm or less.

When FIGS. 11 and 14 in each of which the width of C plane is 0.4 mm are compared, the critical angle for satisfying the total reflecting conditions is changed by changing the refractive index (or wavelength of the laser beam (because the refractive index of the transparent substrate is decided by the wavelength of the laser beam)) of the transparent substrate, so that the number of reflecting times on the surfaces can be adjusted. As for the critical angle to satisfy the total reflecting conditions, as a difference between the refractive index of the transparent substrate and that of the external medium (for example, the air) of the transparent substrate is larger, a degree of freedom of the critical angle increases. In accordance with the above, the number of reflecting times on the surfaces also increases. In fact, however, there is a case where the material of the transparent substrate is limited depending on the use. Therefore, ordinarily, the number of reflecting times on the surfaces can be adjusted by properly selecting the wavelength of the laser beam. As a wavelength of the laser beam, the wavelength in which the absorption for the transparent substrate is little is preferable. Since it is influenced on the resolution of the ununiformity, the wavelength of the laser beam is selected in consideration of the following points.

Figure 16:
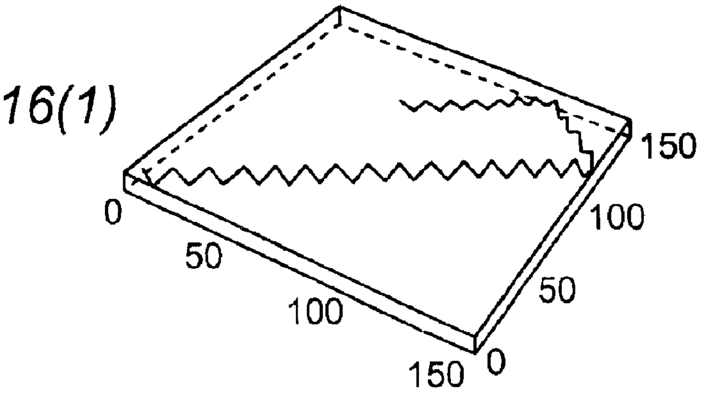
FIG. 16 shows graphs of beam loci showing results of simulating a propagation of the light when a laser beam is introduced to the transparent substrate.
Figure 16:
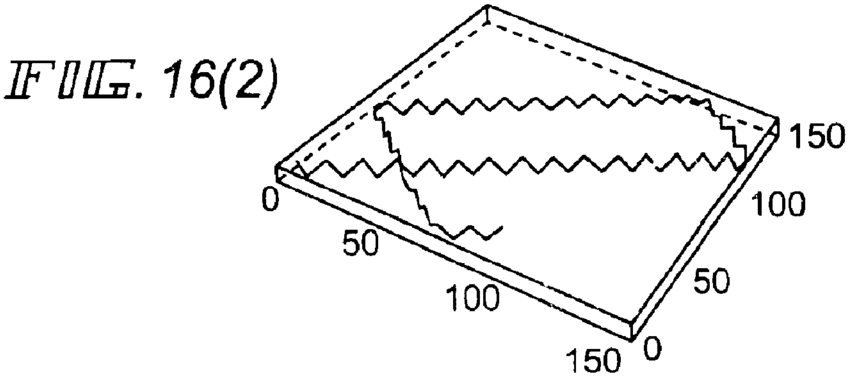
Figure 16:
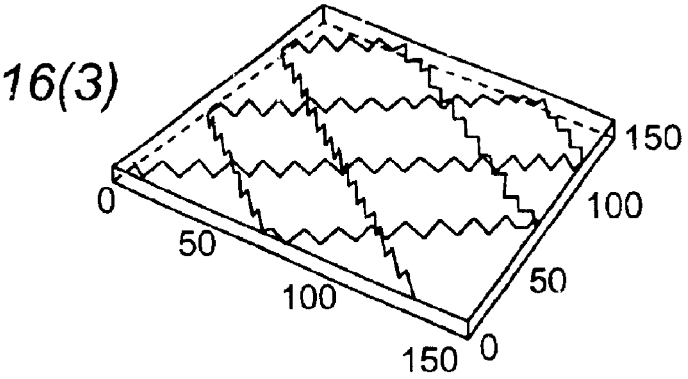
Figure 16:
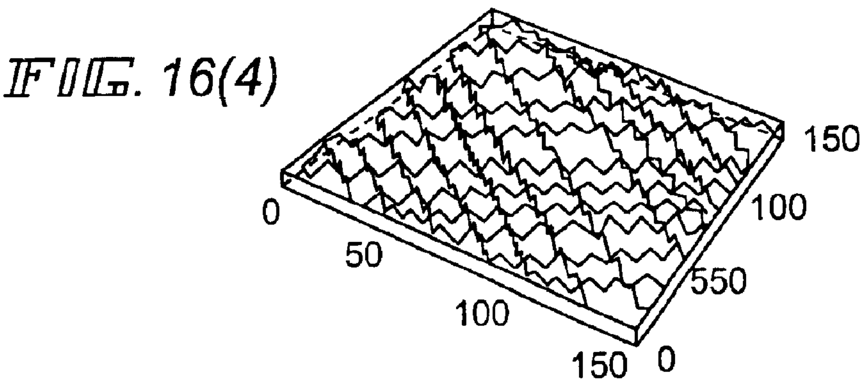

FIG. 16 shows loci of the light beam in the general direction introduced through the transparent substrate, which is not parallel to the one side similar to the above simulation. In the simulation, a vector indicative of the direction of the light beam which impinges on the C plane of the transparent substrate 1 is set to (0.6924, 0.3823, −0.6117) and the conditions other than the above are the same as those of the simulation (FIG. 9). As shown in the diagram, the introduced light beam repeats the total reflection in the transparent substrate 1 and is substantially confined in the substrate, so that the light propagates in the whole area of the substrate. Therefore, even when the scanning of the illuminating light is not executed at all, the whole range of the transparent substrate as an inspecting region can be inspected in a lump at a high speed.

In consideration of the simplification of the inspecting method, the case where one certain surface of the transparent material is decided as shown in the above embodiment, the incident angle satisfying the total reflecting conditions is determined in the surface, the light is introduced, and after that, the incident position of the light is moved in accordance with the form of the transparent material is more preferable than the case where three dimensional directional vectors (x, y, z) of the incident light are set so that the introduced light covers the whole region in the transparent material and the light is introduced from a certain point on the substrate, because the inspecting method can be simplified. When the transparent material is the substrate having the surfaces which face each other, it is particularly effective.

In the above embodiment, the example in which the laser beam was introduced from one side 1*a* of the transparent substrate 1 has been mentioned. The invention is not limited to the above but it is also sufficient that the inspection is executed by introducing the light from the direction of one side 1*b* or from two directions of the sides 1*a* and 1*b*. When the inspection is executed by introducing the light from the two directions of the sides 1*a* and 1*b*, it is effective to detect a defect having directionality or the like and the inspection at a higher precision can be performed, so that it is preferable.

As mentioned above, the present invention is extremely effective with respect to the detection of the defect having directionality for the light, which can be detected because it glints in a specific irradiating direction but cannot be detected because it does not glint in the other irradiating directions, which fact is peculiar to a scratch on glass. The reason is as follows. Since the light is substantially confined in the inspecting object made of the transparent material by geometrically and optically repeating the total reflection, the irradiated light is deviated from an inherent orbit only in the ununiform portion of the inspecting object and leaks out of the inspecting object from the geometrical and optical viewpoints. Even if the only ununiform portion is the defect having directionality for the light, the ununiform portion is illuminated from various directions in the process to repeating the total reflection. In the conventional method, since the light is converged in order to raise the contrast and the light from the one direction is irradiated, even if the defect has a relatively large size, the defect having the directionality can be hardly detected.

Also with regard to the defect of the glass in which the transmittance is the same but the refractive index alone is different, which fact is peculiar to the striae of the glass, the light is deviated from the inherent orbit in a portion where the refractive index is different and leaks out of the inspecting object, so that the defect can be detected. In the conventional method of detecting a light amount such as reflection output or transmission output of the converged light, however, the detection is impossible in principle.

By using the inspecting method of the above-mentioned embodiment, the glass substrate having the defect can be rapidly and properly excluded, so that the productivity of the glass substrate can be improved. By again precisely mirror-polishing and cleaning the glass substrate having the defect such as a scratch on the surface, it can be formed as a glass substrate for the photo mask in a range of a specification.

The above inspecting method is used in the inspecting process after the manufacturing process of the glass substrate as a transparent substrate for the photo mask. There is a variation in size (length or the like) of the glass substrate depending on a difference of the processing precision (ordinarily, a allowance of the transparent substrate for the photo mask has about ±0.4 mm in length and about ±0.1 mm in thickness). Therefore, when variant sizes of the glass substrates are grasped one by one, the optimum total reflecting conditions for each of the glass substrates are obtained, and they are inspected, it takes a long time and it is not practical. Because, when such an inspecting method that the accurate dimensions of the glass substrates are measured, the incident conditions under which the total reflection more occurs are grasped, and after that the laser beam is impinged, an extra time as much as {(time for measuring the dimensions of the glass substrates)+(simulating time)}×(the number of inspecting substrates) is required before the inspection.

In this case, by fluctuating the incident angle of the laser beam which is introduced through the glass substrate in a range where the total reflection is done on the main surfaces (surface and rear surface) and end surfaces (other than the C planes) and the light is reflected between at least the pair of end surfaces and impinging the laser beam, even when there is a variation in dimensions of the glass substrates, the optical ununiformity of the glass substrate can be detected at a high sensitivity and a high speed, so that there are provided ununiformity inspecting method and apparatus of a high utility.

That is, when the optical path in the transparent material is optically uniform, the incident angle is changed in a range where the total reflection may occur on the surface of the transparent material and the light is introduced in the transparent material. Consequently, even when there is a variation in dimensions of the transparent materials and the optimum total reflecting conditions for the transparent materials slightly differ, the incident light of a predetermined direction is not introduced but the light having different incident angles is introduced and propagates various paths while being totally reflected, so that the light is spread up to the corners of the transparent material without leaking.

As fluctuating the incident angle for the substrate, in a manner similar to the angle adjusting means in FIG. 1, a machine which is connected to a computer or the like and which can automatically control the angle is attached to the mirror, an angle adjusting mechanism is provided for the laser itself or the folder for holding the substrate, or means such as an acousto-optical polariscope for fluctuating the incident angle by using the acousto-optical effect of the ultrasonic beam can be also used. As an incident angle to the substrate, for example, in case of the above-mentioned glass substrate (152.4×152.4×6.35 mm) for the photo mask made of quartz glass, it is desirable that the incident angle $\theta i$ of the laser beam is successively changed in a range of 45.0° to 44.0°.

The introduction of the laser beam to the transparent material is performed on the basis of information of the transparent material. Consequently, when a plurality of transparent materials are inspected, particularly, the inspection can be efficiently executed.

In this instance, the information of the transparent material indicates the relative positional relation between the transparent material and illuminating means, the state of the surface of the transparent material (whether it has been mirror-polished), or the like. The information regarding the relative positional relation between the transparent material and the illuminating means is necessary to properly introduce the light from the illuminating means into a predetermined position of the transparent material. When the surface is not in the mirror state, it is difficult to detect the ununiformity of the transparent material. Therefore, the information regarding the surface state of the transparent material can be used when such a substrate is previously eliminated (as necessary, it is returned to the preceding process (polishing or the like)).

By providing position detecting means for detecting the relative positional relation between the transparent material and the illuminating means and transmitting means for transmitting information obtained by the position detecting means to the illuminating means, when a plurality of materials are inspected, the inspection can be efficiently executed. In this instance, the position detecting means indicates a distance measuring device (laser scan measuring system, laser interference measuring device, or the like) by using the laser beam. The transmitting means indicates a computer for fetching data from the position detecting means and feeding back to the illuminating means, the angle adjusting means, moving means for moving the incident position of the introduction light, and the like. It is also sufficient to provide an apparatus such as TV camera or CCD image pickup device image sensor for observing the surface state of the transparent material and, for example, eliminating the inspecting object, for example, which is not mirror-polished.

In the above embodiment, it is desirable to provide discriminating means for discriminating the presence or absence, kind, and size of the ununiformity of the transparent material on the basis of the information of the light detected by the detecting means.

The relation (information) between the presence or absence, kind (scratch or crack of the surface portion, internal striae or foreign matter), and size (area, length, width, depth, region, or the like) of the ununiformity previously existing in the transparent material and the information of the light which leaks out of the surface (light amount, luminance, intensity distribution, depth from the surface of the leak light) has been stored in the computer or the like. By comparing the information of the light detected by the inspection and the stored information, the presence or absence, kind, and size of the ununiformity of the transparent material can be discriminated. By discriminating the presence or absence, kind, and size of the ununiformity of the transparent material, a desired transparent material can be immediately extracted. Consequently, the glass substrate having the ununiformity which has an influence on the time of formation of the pattern or the exposure for a transferring object can be eliminated before the next process after the inspection or can be also returned to the re-polishing process, so that the productivity can be improved.

The discriminating method will now be specifically explained by using the inspecting apparatus in FIG. 1. The light leaked out of the substrate 1 is formed as an image on the surface of the CCD 6 of the CCD camera by the lens system 7. As mentioned above, for a period of time while the laser irradiating region of one line is scanned onto the whole surface of the main surface of the substrate 1, the shutter of the CCD camera is opened as It is and image data of the whole surface of the main surface of the substrate 1 is accumulated. The image data fetched in the CCD camera is converted to a digital signal by the A/D converter 11, the converted signal is inputted to the image processing apparatus 12 and is stored into the storage unit, and an image analysis is performed by the discriminating unit. In the discriminating unit, by comparing the image data of the light detected by the inspection with basic data of the image information which has previously been inputted in the storage unit, the presence or absence, kind, and size of the transparent substrate 1 are discriminated. The moving amount (information of the irradiating position of the substrate 1) of the table 5 or the like is inputted from a laser interferometer (not shown) or the like to the image processing apparatus 12. From the image data of the CCD camera and position data of the substrate 1, which kind and size of ununiform portion exists on which position (x, y) of the substrate 1 is obtained.

Figure 17A:
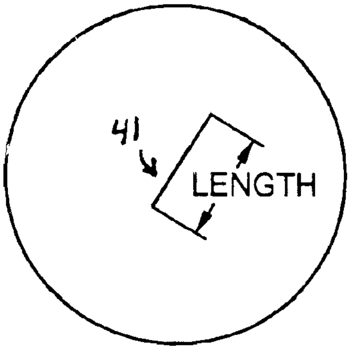
FIG. 17 shows diagrams showing images such as scratches of the transparent substrate observed by an ununiformity inspection of the invention.
Figure 17B:
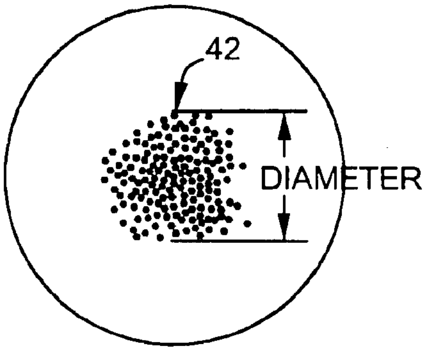

When the ununiform portion exists in the irradiating region of the substrate 1, the ununiform portion (and its periphery) is brightly seen in a dot form. When they are enlarged by the optical microscope, images as shown in FIG. 17 are observed (the images in FIG. 17 are shown by reversing bright and dark of images that are actually observed). A linear image 41 as shown in FIG. 17(*a*) is a scratch on the surface of the substrate 1. As a representative size, the length is 30 μm, the width is 0.2 μm, and the depth is 0.002 μm (the size of such a fine scratch was measured by the atomic force microscope). Many collected images 42 as shown in FIG. 17(*b*) are caused by striae or foreign matters such as gasses in the substrate 1. As a representative size, the diameter is about 1 mm. As mentioned above, since the pattern or size of the image differs depending on the ununiformity existing in the substrate 1, the kind of ununiformity can be discriminated. Further, since the images 42 by the striae are seen so as to glimmer as compared with the image 41 by the scratch, it can be also discriminated from the luminance or intensity distribution of the image.

The size of the ununiform portion can be discriminated from a light amount of the detected light. Further, whether the position where the ununiformity exists is located on the surface portion of the substrate 1 (scratch or clack) or in the substrate 1 (striae or foreign matter) can be discriminated from a location (depth) where a focal point is obtained by focusing on bright dotty portions of the substrate 1 by the optical microscope. As for the inspection of the ununiformity, in order to realize a high speed process, it is desirable that whether the bright dotty leak light exists on the surface of the substrate 1 is first inspected and, with respect to only the substrate 1 in which the leak light was detected, bright dotty portions is further inspected by enlarging or the like by the optical microscope.

Figure 18:
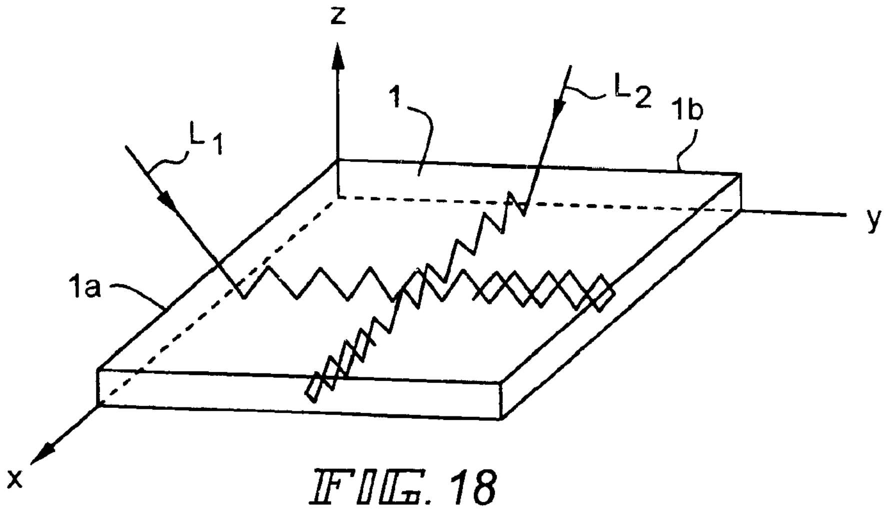
FIG. 18 is a perspective view showing a state when laser beams are introduced from two directions into the transparent substrate.

In order to discriminate the ununiformity, when the light is introduced from the different incident positions and different directions (two directions) to the substrate 1, accurate information of the leak light can be obtained in even case of the ununiformity (defect) having directionality. Consequently, since the presence or absence, kind, and size of the ununiformity can be accurately discriminated, it is preferable. As a method of introducing the light, as shown in FIG. 18, a laser beam L1 is introduced in the direction (X direction) of the side 1*a* of the transparent substrate 1 and a laser beam L2 is introduced in the direction (Y direction) of the side 1*b* at the same time or it is also sufficient that the laser beams of the different directions are introduced every direction (X and Y directions or the like) to the substrate 1, thereby inspecting.

Figure 19:
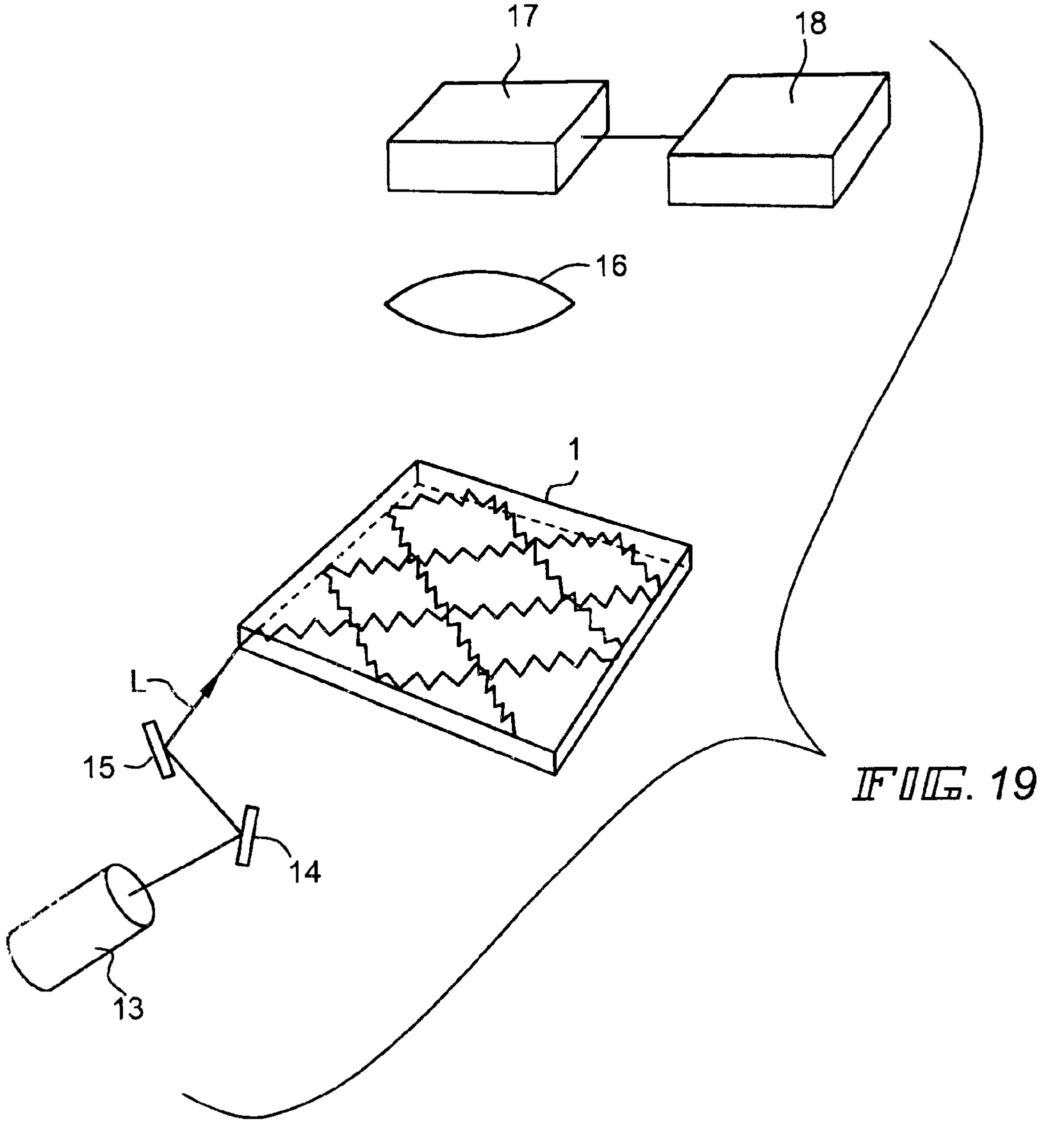
FIG. 19 is a schematic constructional diagram showing an embodiment in which the laser beam is introduced from a corner portion of the transparent substrate.

As shown in FIG. 19, when the ununiformity is inspected by introducing a laser beam L from the corner portion of the transparent substrate 1 by using, for example, a laser 13 and mirrors 14 and 15, the kind and size of the ununiformity can be discriminated by an image forming optical system 16, a CCD camera 17, and an image processing apparatus 18 in a manner similar to the above.

Figure 20:
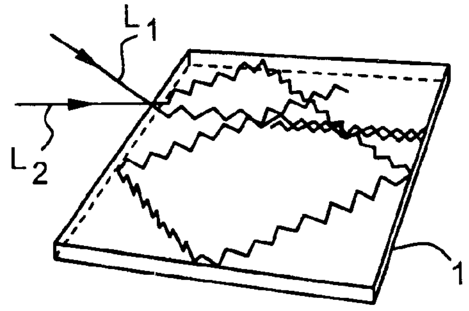
FIG. 20 is a perspective view showing an embodiment in which laser beams are introduced from the same incident position in a plurality of different directions in the transparent substrate.

In the above embodiment, although the example in which the inspection was performed by introducing the laser beam in only the y direction of the substrate 1 has been mentioned, when the laser beam is introduced from the different incident positions and different directions to the substrate 1, it is not necessarily that the incident positions are made different. For example, as shown in FIG. 20, even when the laser beams L1 and L2 are introduced from the same incident position of the substrate 1 to a plurality of different directions as observed from the main surface side of the substrate 1, the effect of the invention that the ununiformity having directionality can be certainly detected can be accomplished.

Although the introduction of the laser beam to the transparent substrate has been performed from the chamfer portion as a C plane in the above embodiment, it is also possible to introduce the beam from planes other than the chamfer portions. In this case, it is sufficient that as an entrance window to introduce the laser beam, an optical member made of a material having substantially the same refractive index as that of the transparent substrate is attached by an adhesive agent or the like. In order to simplify the inspecting method and inspect the ununiformity of the whole region in the transparent substrate by repeating the total reflection more, it is desirable to introduce the laser beam from the chamfer portion as a C plane. The reason is that when the optical member having the entrance window to introduce the laser beam is attached, the light propagated in the transparent substrate does not satisfy the total reflecting conditions in a portion of the optical member, so that the light leaks out of the portion. It is preferable that the chamfer portion is mirror-polished. As the width of chamfer portion is smaller, it is more desirable. It is better to set the width to be equal to 0.4 mm or less, more preferably, 0.2 mm or less. Even if it is set to be extremely small (smaller than 0.1 mm), since a defect occurs upon mirror-polishing, it is not preferable.

Figure 21:
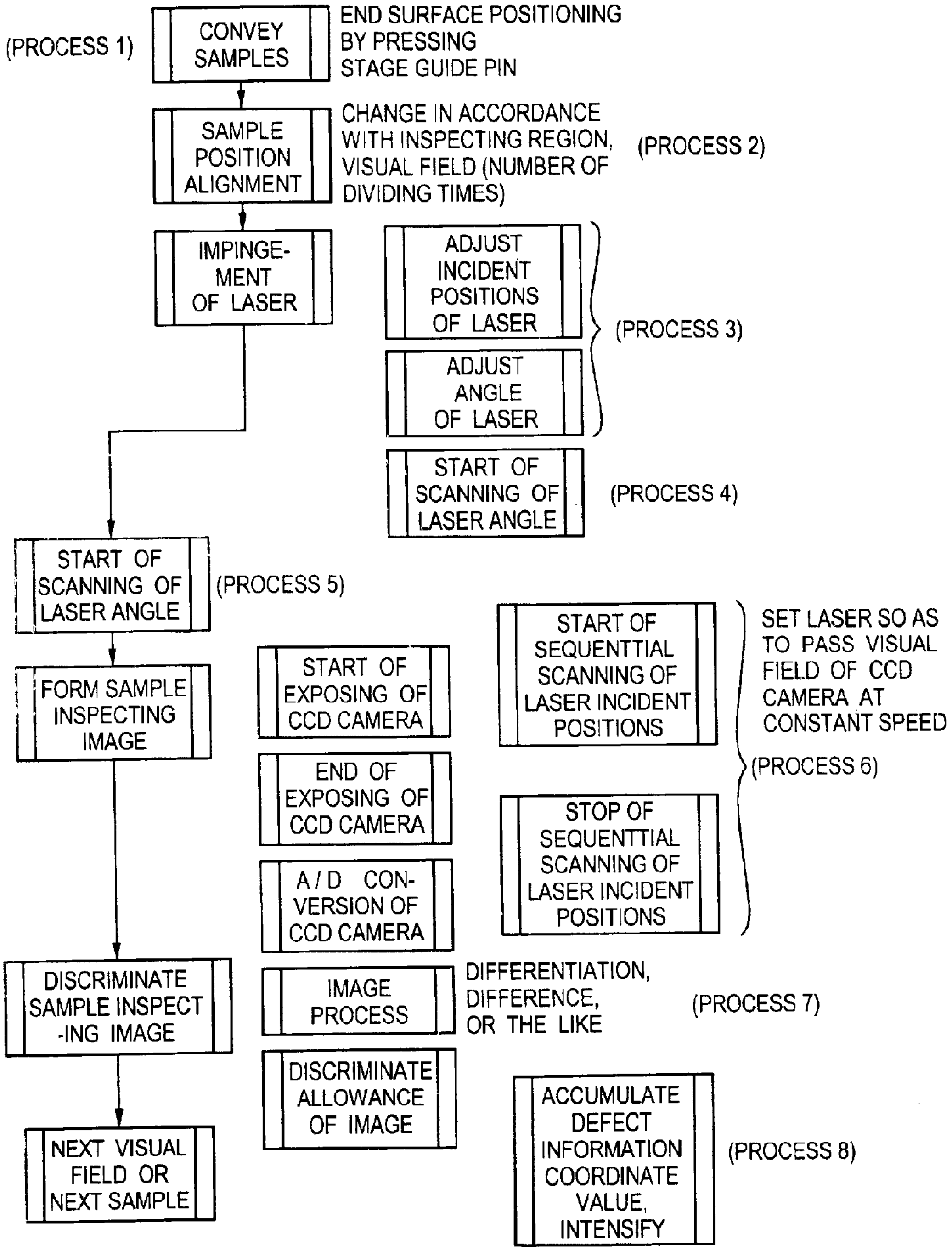
FIG. 21 is a flowchart showing an embodiment of an inspecting processes for separating good and bad transparent substrates from each other.

A method of selecting the transparent substrate which can be used for various uses by using the inspecting method and inspecting apparatus of the invention will now be explained with reference to the drawings. FIG. 21 is a diagram showing a flowchart for the inspecting process to selecting the transparent substrate.

A specific selecting method performed by using the inspecting apparatus in FIG. 1 will now be described with reference to the flowchart for the inspecting process of FIG. 21.

Decision·Alignment of the Inspecting Region

As a transparent substrate 1 serving as an inspecting target, a glass substrate for a photo mask made of quartz glass in which both main surfaces, end surfaces, and chamfer surfaces are mirror-polished, whose size is 152.4×152.4×6.35 mm, and in which the width of each C plane is equal to 0.4 mm is prepared.

The glass substrate is conveyed by conveying means (not shown) until it is come into contact with a stage guide pin (not shown) fixed to a certain reference position of the inspecting apparatus, thereby positioning the glass substrate (process 1). At that time, an origin and coordinates in the glass substrate are decided.

The inspecting region is specified on the basis of the previously decided coordinates. The inspecting region does not always coincide with a measuring visual field of the CCD. Therefore, when they don't coincide with each other, the measuring region is divided into (A1, A2, A3, B1, B2, B3, . . . ) in correspondence to the visual field of the CCD (FIG. 22) (process 2). In this instance, the divided measuring regions A1, A2, A3, B1, B2, B3, . . . coincide with the measuring visual field of the CCD. The CCD used for the measurement is the CCD of the interline system (having no mechanical shutter) having a thermoelectric cooling function is mounted, in which the number of elements is 1300×1035 and a detecting area is 8.71×6.90 mm. The measuring visual field is measured at a magnification of 0.7 time.

The incident position and the incident angle of the laser beam are adjusted so that the laser beam propagates in the inspecting area (process 3). As for the incident position and incident angle of the laser beam, information of the glass substrate is obtained by position detecting means (not shown) for detecting the relative positional relation between the transparent substrate and the laser and the laser beam is introduced by adjusting the mirrors and table so that the laser beam can be accurately introduced through the glass substrates having different sizes. As for the incident angle, since the refractive index of the glass substrate is 1.46 and the critical angle θc is about 43.2°, the incident angle θi is set to 45.0°.

When the laser beam is introduced into the glass substrate, the incident angle of the laser beam is fluctuated in a range where the beam repeats the total reflection and propagates (process 4). In the procedure for inspecting a plurality of glass substrates, even if the respective glass substrates have a little variation in sizes depending on a difference between the processing precisions, since the beam locus propagating in the glass substrate is deviated little by little by changing the incident angle of the light, the process is executed in order to absorb the variation of processing precisions of the glass substrate and inspect the ununiformity of the glass substrate. The process is also executed for an image matching of the CCD in the next process. As means for fluctuating the incident angle, means having a function for automatically adjusting the angle of the mirror by a control of a computer or the like or means such as an acousto-optical polariscope for fluctuating the incident angle by using the acousto-optical effect of the ultrasonic beam can be also used. As a fluctuation of the incident angle, the incident angle θi is successively changed in a range of 45.0° to 44.0° so as to satisfy the total reflection.

In order to precisely discriminate the light which leaks out of the transparent substrate, namely, the ununiformity, the focusing of the CCD image is executed (process 5). The focusing is executed by integratedly moving the laser and the mirrors in an a axial direction (direction to the lens and CCD). It is also sufficient that the glass substrate, mirrors, and laser are fixed and the lens and CCD are integratedly moved in a z axial direction.

Inspection of Ununiformity in Inspecting Region

Figure 22:
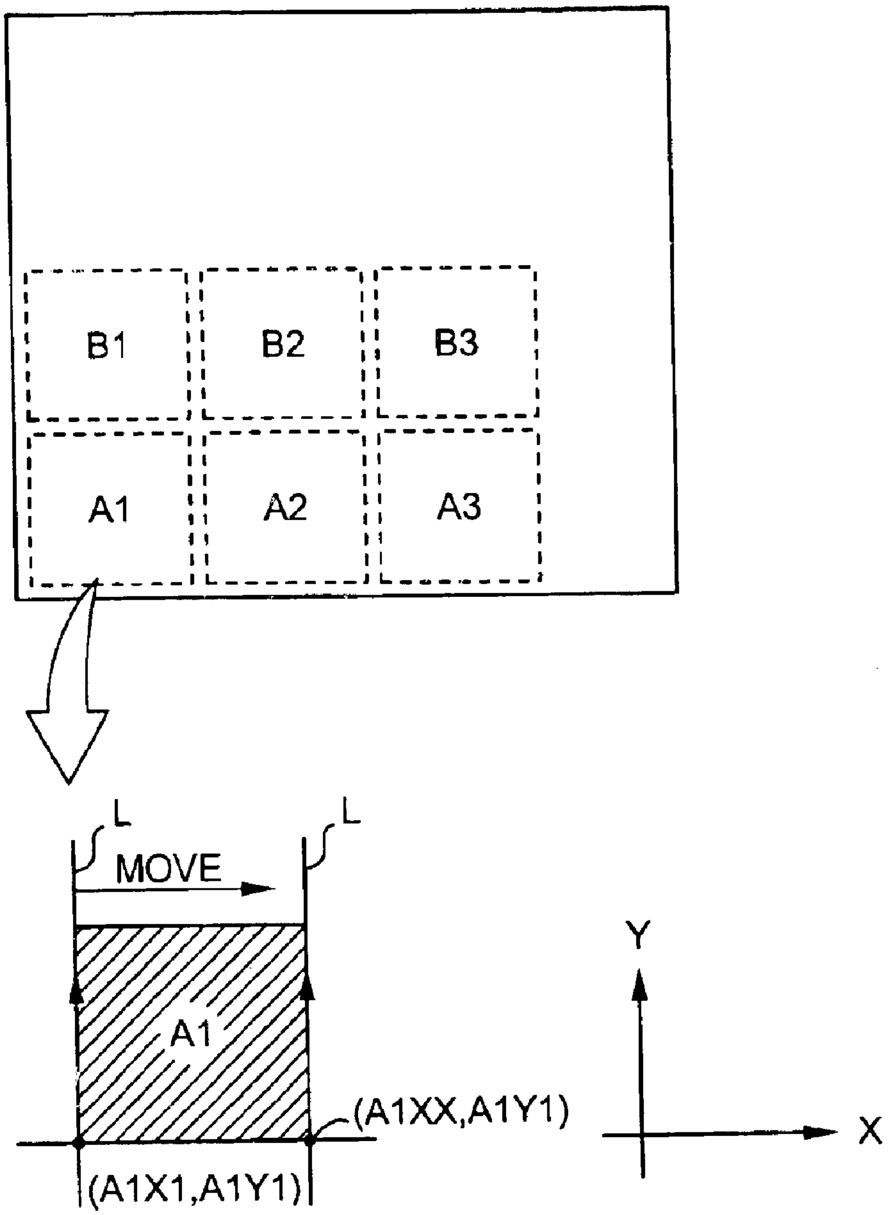
FIG. 22 is a diagram for explaining the first embodiment in which a method of selecting a transparent substrate according to the invention is applied to a glass substrate for a photo mask.

As shown by enlarging one part in FIG. 22, the laser beam L is introduced from the chamfer plane serving as an introducing surface so that the laser beam L which passes certain coordinates (A1X1, A1Y1) of the measuring region A1 as one of the divided regions and is parallel to the y axial direction propagates, the incident angle is changed in a range where the laser beam repeats the total reflection and propagates in the glass substrate (of 45.0° to 44.0°), thereby inspecting the ununiformity. The similar scan is performed so that the laser beam L is moved in the x axial direction, the inspection of the ununiformity is performed until the laser beam passes coordinates (A1X1, A1Y1) at the end portion of the measuring region A1, so that the inspection of the ununiformity in the measuring region A1 is finished (process 6). The exposure of the CCD is executed from the start to the completion of the inspection of the ununiformity in the measuring region A1. As for the inspection of the ununiformity in the measuring region A1, it is also sufficient that the laser beam is impinged so that the laser beam which passes (A1X1, A1Y1) and is parallel to the x axial direction propagates and it is moved in the y axial direction. It is also sufficient to combine and introduce the laser beams in the two directions which cross at right angles to each other. As mentioned above, in case of introducing the light of a plurality of different directions as observed from the main surface side, the light is irradiated into the glass substrate from the plurality of directions. Even when the ununiformity (defect) having directionality exists, it can be accurately detected.

Image Process

Figure 23:
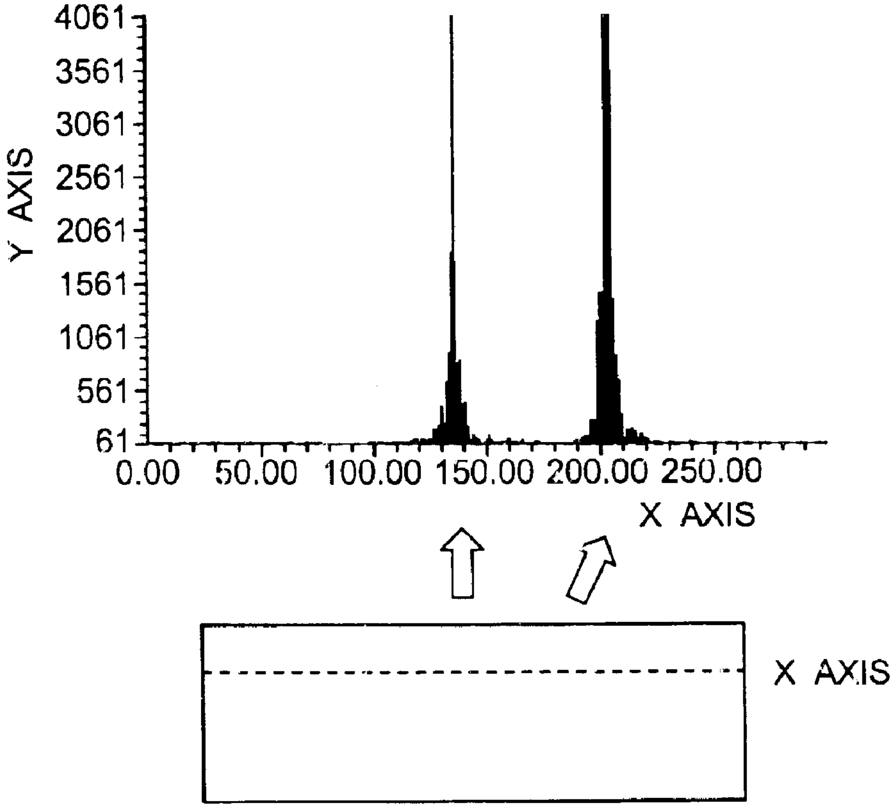
FIG. 23 is a diagram showing a light intensity distribution in the width direction of a scratch obtained from light information of an image of the scratch on the surface of the glass substrate detected by the inspection of the first embodiment in FIG. 22 by the image process.

In the process 6, information (analog signal) of the light which was detected by the CCD and which leaked out of the glass substrate is converted into a digital signal by the A/D converter in order to execute an image process by information accumulating means such as a computer. The information of the light converted into the digital signal is accumulated by the information accumulating means such as a computer, the intensity of the light as shown in FIG. 28 is resolved to 12 bits (4096:1), and the image process is performed (process 7). The Y axis in FIG. 23 denotes the intensity of the light and one scale denotes (20000/4095)·Y (Y:scale) electrons.

Discrimination of Allowance of Ununiformity

As a result of the image process of the process 7, the ununiformity existing in the glass substrate is discriminated as a scratch on the substrate surface. When it is compared with (20000/4095)×200 electrons which has previously been set as an allowance design value of the scratch (when the background is (20000/4095)×100 electrons or less), since it exceeds the allowance design value, it is discriminated that the glass substrate is bad (process 8).

In the embodiment, since the scratch exceeding the allowance range is found on the substrate surface in the inspecting area A1, the inspection for the ununiformity is not executed in the next inspecting area A2 but the process is shifted to the re-polishing and cleaning process for the substrate. When no ununiformity is found in the inspecting region A1, the previously divided inspecting regions A2, A3, B1, B2, . . . and the processes 6 to 8 (according to circumstances, processes 2 to 8) are repetitively executed. When it is discriminated that the ununiformity is equal to the allowance design value or lower in the whole inspecting region, the glass substrate for the photo mask is selected as good.

By using the selecting method of the embodiment, the glass substrate having the defect can be rapidly and properly eliminated, so that the producibility of the glass substrate can be improved. By again precisely mirror-polishing and cleaning the glass substrate having the defect, it can be formed as a glass substrate for the photo mask which lies in the range of the specification.

Figure 24:
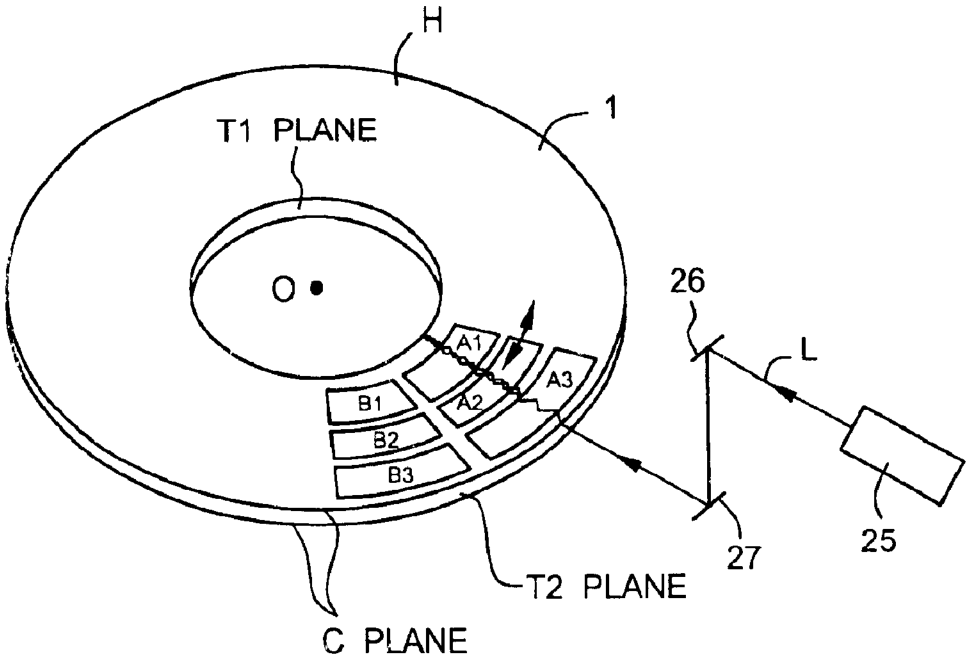
FIG. 24 is a diagram for explaining the second embodiment in which the method of selecting the transparent substrate according to the invention is applied to a glass substrate for a magnetic disk.

FIG. 24 is the second embodiment in which the method of selecting the transparent substrate of the invention is applied to a glass substrate for a magnetic disk. The explanation for the processes overlapped in the first embodiment in which the method is applied to the glass substrate for the photo mask is omitted.

As a transparent substrate 1 serving as an inspecting target, a disc-shaped glass substrate for magnetic disk made of quartz glass in which both main surfaces (H), inner rim edge surface (T1 plane) and outer rim edge surface (T2 plane), and chamfer surfaces (C planes) are mirror-polished and in which the diameter is 95 mm (3.5 inches$\phi$), the thickness is 0.8 mm, and a diameter of a circular hole on a center portion is 20 mm $\phi$ is prepared.

As inspecting regions, as shown in FIG. 24, the region on the main surface of the transparent substrate is divided into the measuring regions A1, A2, A3, . . . from the inner rim side to the outer rim side. The inspection regarding the ununiformity is executed every divided measuring region.

Figure 25:
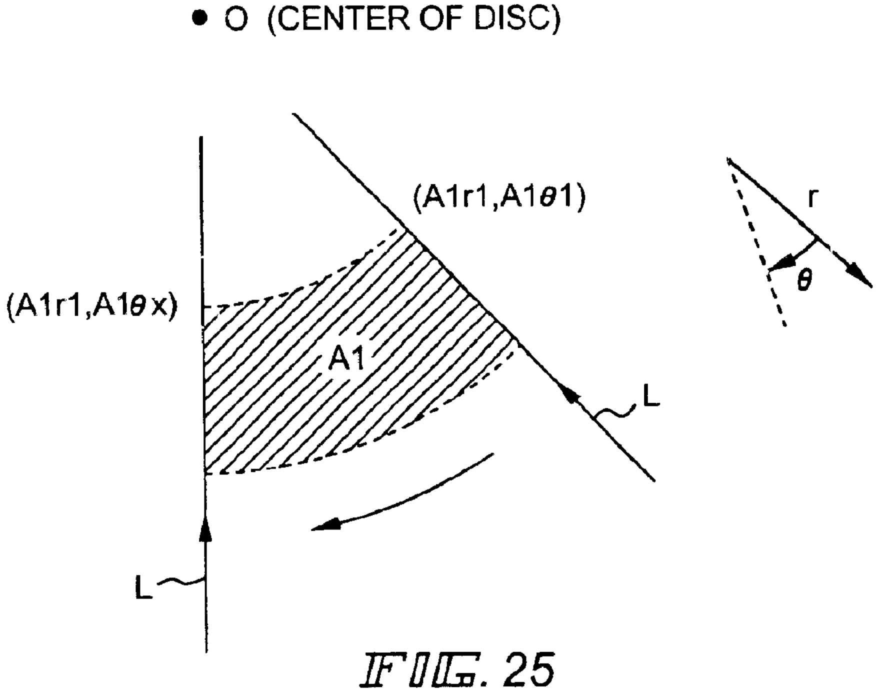
FIG. 25 is a diagram for explaining an inspecting method of the second embodiment of FIG. 24.

The inspection for the ununiformity is executed in such a manner that the laser beam L is introduced from the outer rim edge surface-of the disc-shaped glass substrate 1 in the direction of the center (O) of the disc, the light is confined in one plane in the radial direction (r direction) including the outer rim edge surface and the inner rim edge surface (so that the total reflection is repeated in both the main surfaces of the transparent substrate and the light is returned between the inner rim and outer rim edge surfaces), the disc is rotated by a driving apparatus (not shown) for rotating the disc, and the laser beam L is moved in the direction to the rim ($\theta$ direction) of the disc. Specifically explaining with reference to FIG. 25, the laser beam L is introduced to the chamfer surface (C plane) as an introducing surface by a laser 25 and mirrors 26 and 27 so that the laser beam L which passes certain coordinates (A1r1, A1θ1) of the measuring region A1 divided as shown in FIG. 25 and is parallel to the r direction is propagated, the incident angle is changed in a range (45.0° to 44.0°) where the beam repeats the total reflection and propagates in the disc-shaped glass substrate 1, thereby inspecting the ununiformity. The disc-shaped glass substrate 1 is rotated, the same scan is performed by moving the laser beam in the $\theta$ direction, and when the inspection for the ununiformity in the region which passes the coordinates (A1r1, A1θX) of the measuring region A1 is finished, the inspection of the ununiformity in the measuring region A1 is completed. In the inspection for the ununiformity, it is also sufficient that the laser beam is impinged from the inner rim edge surface of the disc or from both of the inner rim and outer rim edge surfaces.

In a manner similar to the first embodiment, the image process and allowance discrimination for the ununiformity are executed. Consequently, since the defect exceeding the allowance range is not found in the inspecting region A1, the inspecting region is changed to the inspecting regions A2, A3, B1, B2, . . . and the inspection for the ununiformity similar to that in the inspecting region A1 is executed. Although the inspection for the ununiformity is performed in the whole region of the disc-shaped glass substrate, no defect exceeding the allowance range is found, so that it is discriminated as good.

In a manner similar to the first embodiment, when the defect exceeding the allowance range is found in the certain inspecting region, it is discriminated as bad and the process can be also shifted to the re-polishing and cleaning processes for the substrate without executing the inspection for the ununiformity in the following inspecting region.

In the above-mentioned inspecting method and selecting method, as unnecessary light which leaks out of the ununiformity (defect) of the transparent material and which allows the contrast of the light to be decreased, Rayleigh scattering light which scatters due to a microscopic fluctuation of a density that is peculiar to the transparent material or the like exists. In order to reduce the unnecessary light, at least two light having different wavelengths are introduced into the transparent material or light having a specific polarization is introduced, so that the contrast of the detection light for the ununiformity is improved and the detection can be realized at a higher sensitivity and a higher precision. In the former case of introducing at least the two light having different wavelengths, since the Rayleigh scattering light becomes light having a color obtained by mixing the light having different wavelengths, the scattering light can be eliminated by applying a (color) filter for absorbing or reflecting a wavelength area of the mixed light between the transparent material and the detecting means. In the latter case of introducing the light having the specific polarization, the light becomes light having peculiar polarizing characteristics in a peculiar polarizing state by the Rayleigh scattering. By using a difference between the polarizing characteristics and those of light which leaks by the ununiformity, a polarizing device such as polar screen, polarizing plate, or polarizing prism is placed between the transparent material and the detecting means, so that the Rayleigh scattering light can be effectively eliminated.

As unnecessary light which decreases the contrast of the light that leaks out of the ununiformity (defect) of the transparent material, there is stray light derived in such a manner that light which was not introduced in the transparent material is reflected on the surface of the transparent material and is impinged on the detecting system for detecting detection light for the ununiformity. In order to reduce the stray light, the introduction light is reduced in correspondence to the size of the introducing surface of the transparent material on which the laser beam is impinged by converging the beam by the optical system such as a lens and the introducing surface is shaped into a concave cross section so that the converged laser beam is introduced as almost parallel light into the transparent material from the introducing surface. Consequently, the stray light can be reduced, the contrast of the detection light for the ununiformity can be increased, and the detection can be executed at a high sensitivity and a high precision.

As another factor to reduce the contrast of the light which leaks out of the ununiformity (defect) of the transparent material, as shown in FIG. 26 (in the diagram, (1) is a perspective view and (2) is a cross sectional view), there is a case where the light shielding material is a rectangular plate having main surfaces, end surfaces, and chamfer surfaces, when the ununiformity is inspected by introducing the laser beam L from the introducing surface (chamfer surface (C plane)), the light leaks out of the chamfer surfaces other than the introducing surface and becomes stray light. In this case, portions between the chamfer surfaces other than the chamfer surface which face each other in the progressing direction of the light to introduce the light are connected by an introducing light 50 formed by binding a plurality of optical fibers arranged in the surface direction of the chamfer surfaces, thereby enabling the light which leaks out of the chamfer surfaces to be again introduced through the transparent material. Therefore, the stray light is reduced, the introduced laser beam can be more effectively concentrated to the ununiform portion, so that the contrast is increased and the detection can be realized at a high sensitivity and a high speed.

In the embodiment in the inspecting method and the first and second embodiments in the selecting method, the transparent substrate made of glass has been mentioned as a transparent material having the mirror-polished surfaces. It is not limited to glass but any material, for example, optical plastic such as acrylic resin or optical crystal such as quartz through which the inspection light can transmit can be used.

In the embodiment in the inspecting method and the first and second embodiments in the selecting method, the example in which the whole surface of the transparent substrate was mirror-polished has been mentioned. It is not limited to the above but a transparent substrate having a part or whole of the surface which is not mirror-polished can be also used. For example, in case of the glass substrate as a glass substrate for the photo mask, there is a case where the end surfaces other than the main surfaces, in which the pattern is not formed, are not mirror-polished. In case of the glass substrate for the magnetic disk, there is a case where the inner rim and outer rim edge surfaces in which a film such as a magnetic layer is not formed are not mirror-finished. In this case, by coating a liquid such as a matching oil onto the surfaces which are not mirror-finished, the surfaces look as if they are mirror-polished (free surface of liquid, pseudo mirror surface), so that the ununiform portion can be inspected by the inspecting method and inspecting apparatus of the invention. More particularly, when it is desired that the ununiform portion alone (striae, bubbles, foreign matter, or the like) existing in the transparent material is inspected at a stage where the mirror-finishing is not executed, it is effective.

As a liquid which is coated in order to form the pseudo mirror surface, a matching oil or a sealing agent used for optical parts, or masking agent for scratch of the glass can be mentioned. The liquid coated on the surface of the transparent substrate can be in a liquid state as it is or in a solid state of jelly, a hard film, or the like after completion of the coating. As a coating method of the liquid, any method such as brush coating (a brush or a sponge-like material is soaked in liquid, thereby coating), spray coating, or spin coating which can smoothly coat on the surface of the transparent material can be used. In this case, the proper method is selected in accordance with the liquid which is used or coating surface.

When the refractive index of the transparent material is substantially the same as that of the liquid, the liquid-coated surface in a mirror state optically and substantially becomes the surface of the transparent material, so that the light introduced through the transparent material can be certainly totally reflected and be returned into the inside. Specifically speaking, since quartz glass (refractive index is 1.46) or the like is often used as a transparent substrate, as a liquid whose refractive index is approximate to the above and which can be easily handled, canada balsam (refractive index is 1.52), Enterannew (trade name, refractive index is 1.49), diiodemethane (ethylene iodide, refractive index is 1.74), cedar oil (refractive index is 1.52), liquid paraffin (refractive index is 1.48), Aquatex (trade name, refractive index is 1.4), glycerol (refractive index is 1.46), and the like can be mentioned.

As for a water insoluble material such as canada balsam or Enterannew, the refractive index and viscosity can be adjusted by adding organic solution such as xylene. As for a water soluble material such as glycerol or Aquatex, the refractive index and viscosity can be adjusted by adding water. As a masking agent for scratch of the glass, there is emulsion composition in which polyorganosiloxane and polydiorganosiloxane are main components disclosed in Japanese Patent Application Laid-Open Publication No. 6-4496 (1994) or the like.

As an inspection in the case where the whole surface of the transparent substrate is not mirror-finished, for example, there is a case where the ununiformity alone (striae, bubbles, foreign matter, or the like) in the transparent substrate is inspected. In this case, when the ununiform portion exists In the inside, it results in fatal defect. For example, in case of the glass substrate for a phase shift mask, since the bad one can be eliminated by inspecting at a stage before the mirror-finishing, the costs of manufacturing can be also held down.

The form of the transparent material is not limited to the square (rectangular) or circular substrate but the transparent material can take any form of a block form, a sphere, a column, a cylinder, a polyhedron, and a form having curved surfaces. Particularly, when a substrate having surfaces which face each other, more particularly, a substrate having at least two pairs of parallel planes which face each other (for example, square (rectangular) or circular cone) is used as such an above-mentioned transparent material, the introduced light repeats the total reflection and easily enters a state in which the light is confined in the substrate. In fact, the inspection for the wide region of the transparent material can be simultaneously executed and the inspection can be executed at a high speed. As a substrate, further, the inspection can be applied to various kinds of substrates such as glass substrate for the electronic device (for the photo mask (phase shift mask)), glass substrate for the liquid crystal display, or glass substrate for information recording (such as magnetic disk or optical disk) Since the glass substrate for information recording is disc-shaped, in case of actually inspecting, the laser beam is impinged from the polished outer rim or inner rim edge surface (for example, chamfer portion). When the inspection for both the surfaces of the substrate is needed, it is also sufficient that the detecting means are provided on the upper and lower sides of the substrate, respectively, and both of the substrate surfaces are inspected in a lump.

In the above embodiment, the gas laser (He—Ne laser) has been used as a laser. It is not limited to the above but a laser of a visible area such as a semiconductor laser or, so long as it is absorbed to the transparent substrate by little, an excimer laser of an ultraviolet area, an Nd-YAG laser of an infrared area, a $CO_2$ laser, or the like can be used as a light source for the inspection. Particularly, in case of using the laser of the ultraviolet area (for example, a higher harmonic wave of the excimer laser, a YAG laser, or the like), since the foreign matter or the like adhered on the substrate surface can be eliminated due to the operation such as evaporating or transpiring, it is preferable.

In the above embodiment, the example in which the angle adjusting means for changing the incident angle for the substrate was attached to the mirrors located between the laser and the substrate has been mentioned. So long as the incident angle of the laser beam for the substrate can be changed, any construction can be used. It is also sufficient that the angle adjusting means is provided for the laser itself or it is provided for the folder for supporting the substrate. As for the introduction of the laser beam, it is also sufficient that the light is introduced by using not mirrors in the embodiment but an optical fiber. At that time, it is sufficient that an emitting edge portion of the optical fiber is moved along each side of the substrate by using a guide or the like or an fluctuation is applied to the side of the emitting edge portion of the optical fiber, thereby fluctuating the incident angle.

As described in detail, according to the invention, since the laser beam is confined in the transparent material by using the total reflection as a physical critical phenomenon, the responses to the inspection light in the ununiform and uniform portions of the transparent material become critical and the ununiformity appears as a very clear contrast, so that the ununiformity such as a fine scratch can be detected at a high sensitivity and it can be also detected at a high precision and a high speed. Further, not only the ununiformity on the surface of the transparent material but also the defect such as internal damage or striae can be also detected.

The presence or absence, kind, and size of the ununiformity of the transparent material are discriminated on the basis of the information of the light leaked out of the surface of the transparent material, so that a desired transparent material can be immediately extracted and the producibility of the transparent material can be improved.

What is claimed is:

1. A method for inspecting an ununiformity of a transparent material by introducing a laser beam therein;

wherein said transparent material comprises at least one pair of total reflective surfaces arranged so as to face each other in such a manner that the laser beam propagates along said pair of total reflective surfaces with being repeatedly and totally reflected therebetween, at least one pair of turning surfaces arranges so as to face each other in such a manner that the laser beam is turned back when the laser beam is impinged thereagainst, and an introductory surface for introducing the laser beam into said transparent material disposed in a manner to be sandwiched therebetween by at least one of said total reflective surfaces and at least one of said turning surfaces; said total reflective surfaces, said turning surfaces and said introductory surface being mirror-polished;

and wherein when an optical path in said transparent material is uniform, the laser beam is introduced in such a manner that the laser beam which propagates in the transparent material and impinged on said total reflective surfaces and said turning surfaces totally reflects, and in an inspecting region of the transparent material sandwiched by one certain pair of said total reflective surfaces and one certain pair of said turning surfaces, one certain plane in said inspecting region filled with the laser beam by propagating the laser beam in said transparent material is relatively moved in the direction in which the inspecting region is filled with the laser beam for said transparent material; and when an ununiform portion exists in the optical path of the laser beam which is introduced and propagated in said transparent material, light which leaks out of said total reflective surface and/or said returning surfaces is detected, thereby inspecting the ununiformity of the transparent material.

2. The method of claim 1, wherein said transparent material is a glass substrate for an electronic device, and said total reflective surfaces are at least one pair of main surfaces which are parallel to each other, and said turning surfaces are at least one pair of end surfaces which cross said main surfaces, and said introductory surface is a chamfer surface sandwiched by said main surfaces and said end surfaces.

3. The method according to claim 2, wherein the glass substrate for an electronic device is a glass substrate for a photo mask.

4. The method according to claim 2, where in the ununiformity is scratch, crack, stain due to an adhering foreign matter on a surface of the substrate, or internal scratch, crack, bubble, striae of the substrate.

5. The method according to claim 2, wherein a wavelength of the laser beam is set to 1 μm or less.

6. A method for inspecting an ununiformity of a transparent material by introducing a laser beam therein;

wherein said transparent material comprises at least one pair of total reflective surfaces so as to face each other in such a manner that the laser beam propagates along said pair of total reflective surfaces with being repeatedly and totally reflected therebetween, at least one pair of turning surfaces arranged so as to face each other in such a manner that the laser beam is turned back when the laser beam is impinged thereagainst, and an introductory surface for introducing the laser beam into said transparent material disposed in a manner to be sandwiched therebetween by at least one of said total reflective surfaces and at least one of said turning surfaces; said total reflective surfaces, said turning surfaces and said introductory surface being mirror-polished;

and wherein when an optical path is said transparent material is uniform, the laser beam is introduced through a chamfer surface by changing an incident angle thereof within a range where the laser beam totally reflects on said total reflective surfaces and said turning surfaces and repeats between at least one pair of end surfaces in such a manner that the laser beam which propagates in the transparent material and impinges on said total reflective surfaces and said turning surfaces totally reflects, and the laser beam is propagated so as to repeat between at least one pair of said turning surfaces and the laser beam is spread in an inspecting region which is formed by the propagation and is surrounded by said total reflective surfaces and said turning surfaces; and when an ununiform portion exists in the optical path of the laser beam which is introduced and propagate in said transparent material, light which leaks out of said total reflective surface and/or said returning surfaces is detected, thereby inspecting the ununiformity of the transparent material.

7. The method of claim 6, wherein said transparent material is a glass substrate for an electronic device, and said total reflective surfaces are at least one pair of main surfaces which are parallel to each other, and said turning surfaces are at least one pair of end surfaces which cross said main surfaces, and said introductory surface is a chamfer surface sandwiched by said main surfaces and said end surfaces.

8. The method according to claim 7, wherein the glass substrate for an electronic device is a glass substrate for a photo mask.

9. The method according to claim 7, where in the ununiformity is scratch, crack, stain due to an adhering foreign matter on a surface of the substrate, or internal, scratch, crack, bubble, striae of the substrate.

10. The method according to claim 7, wherein a wavelength of the laser beam is set to 1 μm or less.

* * * * *

UNITED STATES PATENT AND TRADEMARK OFFICE

CERTIFICATE OF CORRECTION

PATENT NO. : 6,861,659 B2
APPLICATION NO. : 10/421431
DATED : March 1, 2005
INVENTOR(S) : Masaru Tanabe It is certified that error appears in the above-identified patent and that said Letters Patent is hereby corrected as shown below:

On the Title Page Item (63) under the heading Related U.S. Application Data, "Jul. 16, 1997" should be changed to -- Jul. 16, 1998 --.

Signed and Sealed this
Nineteenth Day of July, 2011

David J. Kappos
*Director of the United States Patent and Trademark Office*